US012780942B2

(12) United States Patent
Nolte et al.

(10) Patent No.: US 12,780,942 B2
(45) Date of Patent: Nov. 3, 2026

(54) ARTC1 LIGANDS FOR CANCER TREATMENT

(71) Applicants: UNIVERSITÄT ZÜRICH, Zürich (CH); UNIVERSITÄTSKLINIKUM HAMBURG-EPPENDORF, Hamburg (DE)

(72) Inventors: Friedrich Nolte, Hamburg (DE); Stephan Menzel, Hamburg (DE); Tobias Suter, Zürich (CH); Michael Hottiger, Zürich (CH); Denise Dorvignit-Pedroso, Zurich (CH); Jesus Glaus-Garzon, Zurich (CH); Kathrin Nowak, Zurich (CH); Fabio Aimi, Zurich (CH)

(73) Assignees: UNIVERSITÄT ZÜRICH, Zürich (CH); UNIVERSITÄTSKLINIKUM HAMBURG-EPPENDORF, Hamburg (DE)

( * ) Notice: Subject to any disclaimer, the term of this patent is extended or adjusted under 35 U.S.C. 154(b) by 973 days.

(21) Appl. No.: 17/995,589

(22) PCT Filed: Apr. 6, 2021

(86) PCT No.: PCT/EP2021/058907
§ 371 (c)(1),
(2) Date: Oct. 6, 2022

(87) PCT Pub. No.: WO2021/204781
PCT Pub. Date: Oct. 14, 2021

(65) Prior Publication Data

US 2023/0151118 A1 May 18, 2023

(30) Foreign Application Priority Data

Apr. 6, 2020 (EP) ..................................... 20168333
May 29, 2020 (EP) ..................................... 20177397

(51) Int. Cl.
*C07K 16/40* (2006.01)
*A61P 35/00* (2006.01)
*C12N 15/113* (2010.01)
*G01N 33/573* (2006.01)

(52) U.S. Cl.
CPC .............. *C07K 16/40* (2013.01); *A61P 35/00* (2018.01); *C12N 15/1137* (2013.01); *G01N 33/573* (2013.01); *C07K 2317/565* (2013.01); *C12N 2310/14* (2013.01); *G01N 2333/91265* (2013.01)

(58) Field of Classification Search
None
See application file for complete search history.

(56) References Cited

PUBLICATIONS

Yang et al (International Journal of Molecular Medicine, 2016, 37:734-742).*
Tang et al (International Journal of Molecular Medicine, 2013, 32:130-136).*
Su et al (International Journal of Molecular Medicine, 2014, 34:842-848).*
McCluskey et al (Clinical Cancer Research, 2005, 11:7929-7937).*
Muckherjee S et al, "ART1, a Mono-ADP-Ribosyltransferase, Regulates Tumor-Infiltrating CD8+ T Cells and Is Highly Expressed in EGFR Mutated Lung Cancers", J. Thor. Oncology,, vol. 15, No. 2s, Feb. 1, 2020 (Feb. 1, 2020), p. s13.
U JX et al., "Effect of ART1 on the proliferation and migration of mouse colon carcinoma CT26 cells in vivo", Mol. Med. Reports., vol. 15, 2017, p. 1222-1228.
Hen C et al, "ART1, an extracellular ADP-ribosyltransferase, is over-expressed in non-small cell lung cancer and facilitates cancer cell survival by immune-mediated mechanisms", J. Thor. Oncol,, vol. 11, No. 2S, Feb. 1, 2016 (Feb. 1, 2016), p. S44.
Ang L et al, "Arginine ADP-ribosyltransferase 1 promotes angiogenesisin colorectal cancer via the PI3K/Akt pathway", Int. J. Mol. Med,, vol. 37, Jan. 1, 2016 (Jan. 1, 2016), p. 734-742.
Li Z. et al., "Expression of ADP-ribosyltransferase 1 Is Associated with Poor Prognosis of Glioma Patients", Tohoku J. Exp. Med., vol. 239, 2016, p. 269-278.
Koch-Nolte F et al, "Use of genetic immunization to raise antibodies recognizing toxin-related cell surface ADP-ribosyltransferases in native conformation", Jul. 1, 2005 (Jul. 1, 2005), vol. 236, No. 1-2, p. 66-71.

* cited by examiner

*Primary Examiner* — Laura B Goddard
(74) *Attorney, Agent, or Firm* — JMB Davis Ben-David

(57) ABSTRACT

The present invention relates to a non-agonist ligand of ARTC1, which inhibits the ADP-ribosyltransferase activity of ARTC1, or an inhibitor nucleic acid sequence capable of downregulating or inhibiting expression of a target nucleic acid sequence encoding ARTC1, for use in prevention or treatment of cancer. The invention also relates to a method for diagnosis of cancer.

8 Claims, 13 Drawing Sheets

Specification includes a Sequence Listing.

E

F

ARTC1 LIGANDS FOR CANCER TREATMENT

CROSS-REFERENCE TO RELATED APPLICATIONS

This is the U.S. National Stage of International Patent Application No. PCT/EP2021/058907 filed on Apr. 6, 2021, which in turn claims the benefit of European Patent Application No. 20168333.1 filed on Apr. 6, 2020, and European Patent application Ser. No. 20/177,397.5 filed on May 29, 2020.

The present invention relates to a non-agonist ligand of ARTC1, particularly a ligand that inhibits the ADP-ribosyltransferase activity of ARTC1 for use in prevention or treatment of cancer. Alternatively, an inhibitor nucleic acid sequence capable of downregulating or inhibiting expression of a target nucleic acid sequence encoding ARTC1 is provided for use in prevention or treatment of cancer.

BACKGROUND

ADP-ribosylation is a post-translational protein modification that has been shown to regulate protein function and gene expression under both physiological conditions and in diseases such as cancer and in inflammation. Protein ADP-ribosylation exists in various forms (monomeric, polymeric) and is added to the peptide/protein in the context of different sequence motifs.

ADP-ribosylation is catalyzed within cells by ARTD family members (structurally related to Diphtheria toxin). The modification at the plasma membrane or in the extracellular space is regulated by ARTC family members (structurally related to *Clostridium* toxin). Four human (ARTC1, 3, 4, 5, formerly also hART1-5) and six mouse ARTC genes (ARTC1, 2.1, 2.2, 3, 4, 5, formerly also mART1-5) have been identified. For both species, ARTC1 is expressed mainly in skeletal and heart muscles, non-lactated mammary gland, brown adipocytes, epithelial cells or activated granulocytes. Although ARTC1 is highly active in vitro, identification of ARTC1 targets in vivo and subsequent characterization of ARTC1-regulated cellular processes on the proteome level has been challenging and only a few ADP-ribosylated targets are known thus far. Therefore, ARTC1-target sites in proteins known to be involved in the regulation of diseases are highly relevant targets for therapeutic intervention of various diseases.

The objective of the present invention is to provide means and methods to treat or prevent cancer. This objective is attained by the subject-matter of the independent claims of the present specification.

SUMMARY OF THE INVENTION

The inventors found the extra-cellular ADP-ribosyl transferase (ART) ARTC1 to be overexpressed in a number of human cancer types (including breast, lung, colon and brain tumors, and many more). Furthermore, they found that ARTC1 modifies proteins on the surface of the tumor and in its microenvironment by transferring ADP-ribose to specific target sites on those proteins. The target proteins include proteins that are involved in tumor growth (growth factor and receptors), vascularization, metastasis and immune regulation (cytokines and their receptors). Thus, the inventors hypothesize that ARTC1 modifies these proteins and thereby their function and thereby generates a microenvironment that favors tumor growth and metastasis. Inhibition of the enzymatic function of ARTC1 or its expression in tumors and at the surface of tumor cells would lead to reduced tumor growth.

A first aspect of the invention relates to a non-agonist ligand of ARTC1 for use in prevention or treatment of cancer.

A second aspect of the invention relates to a nucleic acid molecule for use in prevention or treatment of cancer, comprising, or consisting of, an inhibitor nucleic acid sequence capable of downregulating or inhibiting expression of a target nucleic acid sequence encoding ARTC1.

A third aspect of the invention relates to a method for diagnosis of cancer in a patient, or a method of determining the prognosis of a cancer patient, or a method of assigning a patient to an outcome group, or a method of assigning a patient to a treatment regimen, said method comprising the steps of

- providing an isolated sample of said patient;
- determining the expression level of ARTC1 in said isolated sample; and
- assigning
  - a likelihood of having or developing cancer to said patient, or
  - assigning a likelihood of prognosis to said patient;
  - assigning the patient to an outcome group or
  - assigning the patient to treatment with an anticancer treatment, particularly an anticancer treatment comprising administration of a ligand or nucleic acid as specified in any one of preceding aspects.

A fourth aspect of the invention relates to the non-agonist ligand according to the first aspect of the invention, or the nucleic acid molecule of the second aspect of the invention, for use in prevention or treatment of cancer, wherein a high likelihood of having or developing cancer is assigned to said patient according to the method of the third aspect of the invention.

In another embodiment, the present invention relates a pharmaceutical composition comprising at least one of the compounds of the present invention or a pharmaceutically acceptable salt thereof and at least one pharmaceutically acceptable carrier, diluent or excipient.

DETAILED DESCRIPTION OF THE INVENTION

Terms and Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 4th ed. (2012) Cold Spring Harbor Laboratory Press, Cold Spring Harbor, N.Y. and Ausubel et al., Short Protocols in Molecular Biology (2002) 5th Ed, John Wiley & Sons, Inc.) and chemical methods.

The term adenosine-diphosphate-ribosyl modification (also: ADP-ribosyl modification, ADP-ribosylated peptide, ADP-ribosylated protein) in the context of the present specification relates to a post translational modification (PTM), wherein an ADP-ribose (ADPr) moiety is covalently coupled to an amino acid. This type of post-translational modification is involved in the regulation of various cellular processes including cell signalling, gene regulation, DNA repair and apoptosis.

The term triple-negative breast cancer in the context of the present specification relates to a tumor type not having detectable expression of either one of estrogen receptors, progesterone receptors, or HER2. These tumors are especially difficult to treat, because none of the treatment strategies targeting the estrogen receptor or the progesterone receptor, or approaches making use of HER2-antagonists, can be employed for treatment.

The term mono-ADP-ribosyl modification specifically relates to modifications consisting in a single ADP-ribosyl unit per modification site.

The term specifically reactive in the context of the present invention refers to a property of ligands that bind to their target with a certain affinity and target specificity. The affinity of such a ligand is indicated by the dissociation constant of the ligand. A ligand specifically reactive to a protein has a dissociation constant $K_D$ of $\leq 10^{-7}$ mol/L from its target, but a $K_D$ at least four orders of magnitude higher (i.e. having lower affinity) to a target of similar global chemical characteristics, but a significantly different protein sequence.

The term aptamer relates an oligonucleotide or peptide molecule that binds to a specific target molecule. Aptamers can be created by selecting them from a large random sequence pool. Nucleic acid aptamers can be generated through repeated rounds of in-vitro selection or equivalently, SELEX (systematic evolution of ligands by exponential enrichment) to bind to molecular targets such as small molecules, proteins or nucleic acids through non-covalent interactions. Aptamers offer molecular recognition properties that rival that of antibodies.

The term polypeptide in the context of the present specification relates to a molecule consisting of 50 or more amino acids that form a linear chain wherein the amino acids are connected by peptide bonds. The amino acid sequence of a polypeptide may represent the amino acid sequence of a whole (as found physiologically) protein or fragments thereof. The term "polypeptides" and "protein" are used interchangeably herein and include proteins and fragments thereof. Polypeptides are disclosed herein as amino acid residue sequences.

The term peptide in the context of the present specification relates to a molecule consisting of up to 50 amino acids, in particular 8 to 30 amino acids, more particularly 8 to 15 amino acids, that form a linear chain wherein the amino acids are connected by peptide bonds.

Amino acid residue sequences are given from amino to carboxyl terminus. Capital letters for sequence positions refer to L-amino acids in the one-letter code (Stryer, Biochemistry, $3^{rd}$ ed. p. 21). Lower case letters for amino acid sequence positions refer to the corresponding D- or (2R)-amino acids. Sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, Y), Tyrosine (Tyr, Y), and Valine (Val, V).

The term gene refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

The terms gene expression or expression, or alternatively the term gene product, may refer to either of, or both of, the processes—and products thereof—of generation of nucleic acids (RNA) or the generation of a peptide or polypeptide, also referred to transcription and translation, respectively, or any of the intermediate processes that regulate the processing of genetic information to yield polypeptide products. The term gene expression may also be applied to the transcription and processing of a RNA gene product, for example a regulatory RNA or a structural (e.g. ribosomal) RNA. If an expressed polynucleotide is derived from genomic DNA, expression may include splicing of the mRNA in a eukaryotic cell. Expression may be assayed both on the level of transcription and translation, in other words mRNA and/or protein product.

The term Nucleotides in the context of the present specification relates to nucleic acid or nucleic acid analogue building blocks, oligomers of which are capable of forming selective hybrids with RNA or DNA oligomers on the basis of base pairing. The term nucleotides in this context includes the classic ribonucleotide building blocks adenosine, guanosine, uridine (and ribosylthymine), cytidine, the classic deoxyribonucleotides deoxyadenosine, deoxyguanosine, thymidine, deoxyuridine and deoxycytidine. It further includes analogues of nucleic acids such as phosphotioates, 2'O-methylphosphothioates, peptide nucleic acids (PNA; N-(2-aminoethyl)-glycine units linked by peptide linkage, with the nucleobase attached to the alpha-carbon of the glycine) or locked nucleic acids (LNA; 2'O, 4'C methylene bridged RNA building blocks). Wherever reference is made herein to a hybridizing sequence, such hybridizing sequence may be composed of any of the above nucleotides, or mixtures thereof.

The term siRNA (small/short interfering RNA) in the context of the present specification relates to an RNA molecule capable of interfering with the expression (in other words: inhibiting or preventing the expression) of a gene comprising a nucleic acid sequence complementary or hybridizing to the sequence of the siRNA in a process termed RNA interference. The term siRNA is meant to encompass both single stranded siRNA and double stranded siRNA. siRNA is usually characterized by a length of 17-24 nucleotides. Double stranded siRNA can be derived from longer double stranded RNA molecules (dsRNA). According to prevailing theory, the longer dsRNA is cleaved by an endo-ribonuclease (called Dicer) to form double stranded siRNA. In a nucleoprotein complex (called RISC), the double stranded siRNA is unwound to form single stranded siRNA. RNA interference often works via binding of an siRNA molecule to the mRNA molecule having a complementary sequence, resulting in degradation of the mRNA. RNA interference is also possible by binding of an siRNA molecule to an intronic sequence of a pre-mRNA (an immature, non-spliced mRNA) within the nucleus of a cell, resulting in degradation of the pre-mRNA.

The term shRNA (small hairpin RNA) in the context of the present specification relates to an artificial RNA molecule with a tight hairpin turn that can be used to silence target gene expression via RNA interference (RNAi).

The term sgRNA (single guide RNA) in the context of the present specification relates to an RNA molecule capable of sequence-specific repression of gene expression via the CRISPR (clustered regularly interspaced short palindromic repeats) mechanism.

The term miRNA (microRNA) in the context of the present specification relates to a small non-coding RNA molecule (containing about 22 nucleotides) that functions in RNA silencing and post-transcriptional regulation of gene expression.

The term antisense oligonucleotide in the context of the present specification relates to an oligonucleotide having a sequence substantially complimentary to, and capable of hybridizing to, an RNA. Antisense action on such RNA will lead to modulation, particular inhibition or suppression of the RNA's biological effect. If the RNA is an mRNA, expression of the resulting gene product is inhibited or suppressed. Antisense oligonucleotides can consist of DNA, RNA, nucleotide analogues and/or mixtures thereof. The skilled person is aware of a variety of commercial and non-commercial sources for computation of a theoretically optimal antisense sequence to a given target. Optimization can be performed both in terms of nucleobase sequence and in terms of backbone (ribo, deoxyribo, analogue) composition. Many sources exist for delivery of the actual physical oligonucleotide, which generally is synthesized by solid state synthesis.

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

In the context of the present specification, the terms sequence identity and percentage of sequence identity refer to a single quantitative parameter representing the result of a sequence comparison determined by comparing two aligned sequences position by position. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless stated otherwise, sequence identity values provided herein refer to the value obtained using the BLAST suite of programs (Altschul et al., J. Mol. Biol. 215:403-410 (1990)) using the above identified default parameters for protein and nucleic acid comparison, respectively.

Reference to identical sequences without specification of a percentage value implies 100% identical sequences (i.e. the same sequence).

In the context of the present specification, the term hybridizing sequence encompasses a polynucleotide sequence comprising or essentially consisting of RNA (ribonucleotides), DNA (deoxyribonucleotides), phosphothioate deoxyribonucleotides, 2'-O-methyl-modified phosphothioate ribonucleotides, LNA and/or PNA nucleotide analogues.

In the context of the present specification, the term antibody refers to whole antibodies including but not limited to immunoglobulin type G (IgG), type A (IgA), type D (IgD), type E (IgE) or type M (IgM), any antigen binding fragment or single chains thereof and related or derived constructs. A whole antibody is a glycoprotein comprising at least two heavy (H) chains and two light (L) chains inter-connected by disulfide bonds. Each heavy chain is comprised of a heavy chain variable region ($V_H$) and a heavy chain constant region ($C_H$). The heavy chain constant region of IgG is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system. Similarly, the term encompasses a so-called nanobody or single domain antibody, an antibody fragment consisting of a single monomeric variable antibody domain.

In the context of the present specification, the term humanized antibody refers to an antibody originally produced by immune cells of a non-human species, the protein sequences of which have been modified to increase their similarity to antibody variants produced naturally in humans. The term humanized antibody as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term antibody-like molecule in the context of the present specification refers to a molecule capable of specific binding to another molecule or target with high affinity/a Kd≤10E-8 mol/l. An antibody-like molecule binds to its target similarly to the specific binding of an antibody. The term antibody-like molecule encompasses a repeat protein, such as a designed ankyrin repeat protein (Molecular Partners, Zurich), an engineered antibody mimetic protein exhibiting highly specific and high-affinity target protein binding (see US2012142611, US2016250341, US2016075767 and US2015368302, all of which are incorporated herein by reference). The term antibody-like molecule further encompasses, but is not limited to, a polypeptide derived from armadillo repeat proteins, a polypeptide derived from leucine-rich repeat proteins and a polypeptide derived from tetratricopeptide repeat proteins.

The term antibody-like molecule further encompasses a specifically binding polypeptide derived from a protein A domain, a fibronectin domain FN3, a consensus fibronectin domain, a lipocalin (see Skerra, Biochim. Biophys. Acta 2000, 1482(1-2):337-50), a polypeptide derived from a Zinc finger protein (see Kwan et al. Structure 2003, 11(7):803-813), a Src homology domain 2 (SH2) or Src homology domain 3 (SH3), a PDZ domain, a gamma-crystallin, ubiquitin, a cysteine knot polypeptide or a knottin, cystatin, Sac7d, a triple helix coiled coil (also known as alphabodies), a Kunitz domain or a Kunitz-type protease inhibitor and a carbohydrate binding module 32-2.

The term specific binding in the context of the present invention refers to a property of ligands that bind to their target with a certain affinity and target specificity. The affinity of such a ligand is indicated by the dissociation constant of the ligand. A specifically reactive ligand has a dissociation constant of $\leq 10^{-7}$ mol/L when binding to its target, but a dissociation constant at least three orders of magnitude higher in its interaction with a molecule having a globally similar chemical composition as the target, but a different three-dimensional structure.

A polymer of a given group of monomers is a homopolymer (made up of a multiple of the same monomer); a copolymer of a given selection of monomers is a heteropolymer constituted by monomers of at least two of the group.

As used herein, the term pharmaceutical composition refers to a compound of the invention, or a pharmaceutically acceptable salt thereof, together with at least one pharmaceutically acceptable carrier. In certain embodiments, the pharmaceutical composition according to the invention is provided in a form suitable for topical, parenteral or injectable administration.

As used herein, the term pharmaceutically acceptable carrier includes any solvents, dispersion media, coatings, surfactants, antioxidants, preservatives (for example, antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington: the Science and Practice of Pharmacy, ISBN 0857110624).

As used herein, the term treating or treatment of any disease or disorder (e.g. cancer) refers in one embodiment, to ameliorating the disease or disorder (e.g. slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described hereinbelow.

A first aspect of the invention relates to a non-agonist ligand of ARTC1 for use in prevention or treatment of cancer.

In certain embodiments, the ligand inhibits the ADP-ribosyltransferase activity of ARTC1.

In certain embodiments, the ligand is selected from an antibody, an antibody-like molecule, an aptamer, and an antibody fragment.

In certain embodiments, the non-agonist ligand is selected from an antibody and an antibody-like molecule.

In certain embodiments, the ligand is an antibody or antibody-like molecule and comprises a light chain variable region comprising LCDR1, LCDR2 and LCDR3 and a heavy chain variable region comprising HCDR1, HCDR2 and HCDR3 and a. LCDR1 is a CDR1 comprised in a sequence selected from SEQ ID NO 006, SEQ ID NO 009, SEQ ID NO 012, SEQ ID NO 015 and SEQ ID NO 018;
b. LCDR2 is a CDR2 comprised in a sequence selected from SEQ ID NO 006, SEQ ID NO 009, SEQ ID NO 012, SEQ ID NO 015 and SEQ ID NO 018;
c. LCDR3 is a CDR3 comprised in a sequence selected from SEQ ID NO 006, SEQ ID NO 009, SEQ ID NO 012, SEQ ID NO 015 and SEQ ID NO 018;
d. HCDR1 is a CDR1 comprised in a sequence selected from SEQ ID NO 005, SEQ ID NO 008, SEQ ID NO 011, SEQ ID NO 014 and SEQ ID NO 017;
e. HCDR2 is a CDR2 comprised in a sequence selected from SEQ ID NO 005, SEQ ID NO 008, SEQ ID NO 011, SEQ ID NO 014 and SEQ ID NO 017; and
f. HCDR3 is a CDR3 comprised in a sequence selected from SEQ ID NO 005, SEQ ID NO 008, SEQ ID NO 011, SEQ ID NO 014 and SEQ ID NO 017.

In certain embodiments, the antibody or said antibody-like molecule comprises a light chain variable region comprising LCDR1, LCDR2 and LCDR3 and a heavy chain variable region comprising HCDR1, HCDR2 and HCDR3 and a. said LCDR1 is comprised in, particularly is identical to an LCDR1 reference sequence selected from SEQ ID NO 020, SEQ ID NO 021, SEQ ID NO 022, SEQ ID NO 023 and SEQ ID NO 024 or wherein said LCDR1 is derived from any one of said LCDR1 reference sequences by the substitution rules given below;

b. said LCDR2 is comprised in, particularly is identical to an LCDR2 reference sequence selected from SEQ ID NO 025, SEQ ID NO 026, SEQ ID NO 027, SEQ ID NO 028 and SEQ ID NO 029 or wherein said LCDR2 is derived from any one of said LCDR2 reference sequences by the substitution rules given below, particularly said LCDR2 is comprised in, particularly is identical to an LCDR2 reference sequence selected from SEQ ID NO 050, SEQ ID NO 051, SEQ ID NO 052, SEQ ID NO 053 and SEQ ID NO 054 or wherein said LCDR2 is derived from any one of said LCDR2 reference sequences by the substitution rules given below;

c. said LCDR3 is comprised in, particularly is identical to an LCDR3 reference sequence selected from SEQ ID NO 030, SEQ ID NO 031, SEQ ID NO 032, SEQ ID NO 033 and SEQ ID NO 034 or wherein said LCDR3 is derived from any one of said LCDR3 reference sequences by the substitution rules given below;

d. said HCDR1 is comprised in, particularly is identical to a HCDR1 reference sequence selected from SEQ ID NO 035, SEQ ID NO 036, SEQ ID NO 037, SEQ ID NO 038 and SEQ ID NO 039 or wherein said HCDR1 is derived from any one of said LCDR1 reference sequences by the substitution rules given below;

e. said HCDR2 is comprised in, particularly is identical to a HCDR2 reference sequence selected from SEQ ID NO 040, SEQ ID NO 041, SEQ ID NO 042, SEQ ID NO 043 and SEQ ID NO 044 or wherein said HCDR2 is derived from any one of said HCDR2 reference sequences by the substitution rules given below, particularly said HCDR2 is comprised in, particularly is identical to a HCDR2 reference sequence selected from SEQ ID NO 055, SEQ ID NO 056, SEQ ID NO 057, SEQ ID NO 058 and SEQ ID NO 059 or wherein said HCDR2 is derived from any one of said HCDR2 reference sequences by the substitution rules given below; and f. said HCDR3 is comprised in, particularly is identical to a HCDR3 reference sequence selected from SEQ ID NO 045, SEQ ID NO 046, SEQ ID NO 047, SEQ ID NO 048 and SEQ ID NO 049 or wherein said HCDR3 is derived from any one of said HCDR3 reference sequences by the substitution rules given below.

Substitution Rules

The substitution rules for deriving said LCDR1, LCDR2, LCDR3, HCDR1, HCDR2 and HCDR3 sequences from their respective reference sequence are:

a. glycine (G) and alanine (A) are interchangeable; valine (V), leucine (L), and isoleucine (I) are interchangeable, A and V are interchangeable;
b. tryptophan O) and phenylalanine (F) are interchangeable, tyrosine (Y) and F are interchangeable;
c. serine (S) and threonine (T) are interchangeable;
d. aspartic acid (D) and glutamic acid (E) are interchangeable
e. asparagine (N) and glutamine (Q) are interchangeable; N and S are interchangeable; N and D are interchangeable; E and Q are interchangeable;
f. methionine (M) and Q are interchangeable;
g. cysteine (C), A and S are interchangeable;
h. proline (P), G and A are interchangeable;
i. arginine (R) and lysine (K) are interchangeable.

In particular embodiments, at most two amino acids are exchanged. In more particular embodiments, at most one amino acid is exchanged by the substitution rules given above.

For example, if the LCDR1 of RG4-A111 (RASSSVSYMY) is modified by the substitution rules given above, the resulting modified LCDR1 of RG4-A111 may be RGSSSVSYMY (A to G) or RASTSVSYMY (S to T) or any other sequence resulting from those substitution rules.

In certain embodiments, a. said LCDR1 is selected from SEQ ID NO 020, SEQ ID NO 021, SEQ ID NO 022, SEQ ID NO 023 and SEQ ID NO 024;
b. said LCDR2 is selected from SEQ ID NO 025, SEQ ID NO 026, SEQ ID NO 027, SEQ ID NO 028 and SEQ ID NO 029, particularly said LCDR2 is selected from SEQ ID NO 050, SEQ ID NO 051, SEQ ID NO 052, SEQ ID NO 053 and SEQ ID NO 054;
c. said LCDR3 is selected from SEQ ID NO 030, SEQ ID NO 031, SEQ ID NO 032, SEQ ID NO 033 and SEQ ID NO 034;
d. said HCDR1 is selected from SEQ ID NO 035, SEQ ID NO 036, SEQ ID NO 037, SEQ ID NO 038 and SEQ ID NO 039;
e. said HCDR2 is selected from SEQ ID NO 040, SEQ ID NO 041, SEQ ID NO 042, SEQ ID NO 043 and SEQ ID NO 044, particularly said HCDR2 is selected from SEQ ID NO 055, SEQ ID NO 056, SEQ ID NO 057, SEQ ID NO 058 and SEQ ID NO 059; and
f. said HCDR3 is selected from SEQ ID NO 045, SEQ ID NO 046, SEQ ID NO 047, SEQ ID NO 048 and SEQ ID NO 049.

In certain embodiments, the non-agonist ligand comprises LCDR and HCDR sequences defined as follows:

a. LCDR1 is of sequence SEQ ID NO 020, LCDR2 is of sequence SEQ ID NO 025 or SEQ ID NO 050, LCDR3 is of sequence SEQ ID NO 030, HCDR1 is of sequence SEQ ID NO 035, HCDR2 is of sequence SEQ ID NO 040 or SEQ ID NO 055, and HCDR3 is of sequence SEQ ID NO 045,
b. LCDR1 is of sequence SEQ ID NO 021, LCDR2 is of sequence SEQ ID NO 026 or SEQ ID NO 051, LCDR3 is of sequence SEQ ID NO 031, HCDR1 is of sequence SEQ ID NO 036, HCDR2 is of sequence SEQ ID NO 041 or SEQ ID NO 056, and HCDR3 is of sequence SEQ ID NO 046,
c. LCDR1 is of sequence SEQ ID NO 022, LCDR2 is of sequence SEQ ID NO 027 or SEQ ID NO 052, LCDR3 is of sequence SEQ ID NO 032, HCDR1 is of sequence SEQ ID NO 037, HCDR2 is of sequence SEQ ID NO 042 or SEQ ID NO 057, and HCDR3 is of sequence SEQ ID NO 047,
d. LCDR1 is of sequence SEQ ID NO 023, LCDR2 is of sequence SEQ ID NO 028 or SEQ ID NO 053, LCDR3 is of sequence SEQ ID NO 033, HCDR1 is of sequence SEQ ID NO 038, HCDR2 is of sequence SEQ ID NO 043 or SEQ ID NO 058, and HCDR3 is of sequence SEQ ID NO 048, or
e. LCDR1 is of sequence SEQ ID NO 024, LCDR2 is of sequence SEQ ID NO 029 or SEQ ID NO 054, LCDR3 is of sequence SEQ ID NO 034, HCDR1 is of sequence SEQ ID NO 039, HCDR2 is of sequence SEQ ID NO 044 or SEQ ID NO 059, and HCDR3 is of sequence SEQ ID NO 049.

In certain embodiments, the non-agonist ligand comprises a. a first sequence at least 90% identical, particularly ≥94%, ≥96% or even ≥98% identical to one of SEQ ID NO 006, SEQ ID NO 009, SEQ ID NO 012, SEQ ID NO 015 and SEQ ID NO 018; and b. a second sequence at least 90% identical, particularly ≥94%, ≥96% or even ≥98% identical to one of SEQ ID NO 005, SEQ ID NO 008, SEQ ID NO 011, SEQ ID NO 014 and SEQ ID NO 017.

In certain embodiments, the non-agonist ligand comprises a sequence at least 90% identical, particularly ≥94%, ≥96% or even ≥98% identical to one of SEQ ID NO 007, SEQ ID NO 010, SEQ ID NO 013, SEQ ID NO 016 and SEQ ID NO 019.

In certain embodiments, the non-agonist ligand is characterized in being able to prevent ADP-ribosylation of RR, RG, GR, RXR and GXXXXR motifs.

In certain embodiments, the non-agonist ligand is characterized in that it is specifically reactive against a polypeptide encoded by any one of SEQ 001, SEQ 002, SEQ 003 or SEQ 004.

A second aspect of the invention relates to a nucleic acid molecule for use in prevention or treatment of cancer. The nucleic acid molecule according to this aspect of the invention comprises, or consists of, an inhibitor nucleic acid sequence capable of downregulating or inhibiting expression of a target nucleic acid sequence encoding ARTC1.

In certain embodiments, the inhibitor nucleic acid sequence is an antisense oligonucleotide, an siRNA, an shRNA, an sgRNA or an miRNA.

In certain embodiments of the first or second aspect, the ligand (particularly the antibody or antibody-like molecule) or nucleic acid is administered in treatment of a cancer is selected from breast cancer, colon cancer, lung cancer, liver cancer, glioma, kidney cancer, testis cancer, pancreas cancer, sarcoma, melanoma, prostate cancer, stomach cancer, ovary cancer, bladder cancer, uterus cancer, endometrioid adenocarcinoma, thyroid papillary carcinoma, cervix squamous carcinoma, esophageal cancer, Ewing sarcoma, thyroid anaplastic carcinoma, chordoma, chondrosarcoma, ocular melanoma, pseudomyxoma peritonei, and urachal carcinoma.

In certain particular embodiments, the treatment is for cancer selected from breast cancer, colon cancer, lung cancer, liver cancer, glioma, kidney cancer, testis cancer, pancreas cancer, sarcoma, melanoma, and prostate cancer.

In certain particular embodiments, the treatment is for cancer selected from breast cancer, lung cancer, kidney cancer and glioma. In certain more particular embodiments, the cancer is breast cancer. In certain even more particular embodiments, the cancer is triple-negative breast cancer.

A third aspect of the invention relates to a method for diagnosis of cancer in a patient, or a method of determining the prognosis of a cancer patient, or a method of assigning a patient to an outcome group, or a method of assigning a patient to a treatment regimen. The method according to this aspect of the invention comprises the steps of providing an isolated sample obtained from said patient;

determining an expression level of ARTC1 in said isolated sample; and assigning

- a likelihood of having or developing cancer to said patient, or
- assigning a likelihood of prognosis to said patient;
- assigning the patient to an outcome group or
- assigning the patient to treatment with an anticancer treatment, particularly an anticancer treatment comprising administration of a ligand or nucleic acid as specified in any one of preceding aspects.

In certain embodiments,

- a high likelihood of having or developing cancer is assigned to said patient, or
- a more severe prognosis is assigned to said patient; or
- treatment with an anticancer treatment is assigned to said patient;

if more than 0.5%, particularly more than 1%, more particularly more than 2%, most particularly more than 5% of the cells in said isolated sample of said patient are stained positive for ARTC1.

The term more severe in the context of the present specification relates to a prognosis of a higher likelihood of having or developing a more aggressive form of cancer.

The term stained positive for ARTC1 in the context of the present specification relates to expression of an antigen assayed by an antibody, which can be detected. This may be done by, but is not limited to, staining of a histological tissue slice with an ARTC1 antibody and a labelled secondary antibody.

A fourth aspect of the invention relates to the non-agonist ligand of the first aspect or the nucleic acid molecule of the second aspect for use in prevention or treatment of cancer, wherein a high likelihood of having or developing cancer is assigned to said patient according to the method of the third aspect.

Medical Treatment, Dosage Forms and Salts

Similarly, within the scope of the present invention is a method of treating cancer in a patient in need thereof, comprising administering to the patient a ligand (particularly an antibody or antibody-like molecule) or a nucleic acid molecule according to the above description.

In certain embodiments, the non-agonist ARTC1 polypeptide ligand is an antibody, antibody fragment, an antibody-like molecule or a protein A domains derived polypeptide.

In some embodiments, the non-agonist ARTC1 polypeptide ligand is an immunoglobulin consisting of two heavy chains and two light chains. In some embodiments, the non-agonist anti-ARTC1 polypeptide ligand is a single domain antibody, consisting of an isolated variable domain from a heavy or light chain. In some embodiments, the non-agonist anti-ARTC1 polypeptide ligand is a heavy-chain antibody consisting of only heavy chains such as antibodies found in camelids.

In certain embodiments, the non-agonist ARTC1 polypeptide ligand is an antibody fragment. In certain embodiments, the non-agonist ARTC1 polypeptide ligand is a Fab fragment, i.e. the antigen-binding fragment of an antibody, or a single-chain variable fragment, i.e. a fusion protein of the variable region of heavy and the light chain of an antibody connected by a peptide linker.

Similarly, a dosage form for the prevention or treatment of cancer is provided, comprising a non-agonist ligand or antisense molecule according to any of the above aspects or embodiments of the invention.

Dosage forms may be for parenteral administration, such as subcutaneous, intravenous, intrahepatic or intramuscular injection forms. Enteral administration forms are encompassed where appropriate, such as nasal, buccal, rectal, transdermal or oral administration forms, or as an inhalation form or suppository. Optionally, a pharmaceutically acceptable carrier and/or excipient may be present.

Method of Manufacture and Method of Treatment According to the Invention

The invention further encompasses, as an additional aspect, the use of a non-agonist ARTC1 ligand or a nucleic acid molecule as identified herein, or its pharmaceutically acceptable salt, as specified in detail above, for use in a method of manufacture of a medicament for the treatment or prevention of cancer.

Similarly, the invention encompasses methods of treatment of a patient having been diagnosed with cancer. This method entails administering to the patient an effective amount of a non-agonist ARTC1 ligand or a nucleic acid molecule as identified herein, or its pharmaceutically acceptable salt, as specified in detail herein.

The invention further encompasses the use of determining an expression level of ARTC1 identified herein for use in the manufacture of a kit for the detection of cancer. This aspect of the invention relates to a system for performing the method for diagnosis of cancer in a patient, or the method of determining the prognosis of a cancer patient, or the method of assigning a patient to an outcome group, or the method of assigning a patient to a treatment regimen according to the third aspect.

Similarly, the invention encompasses a method for treating a tissue sample, using a ARTC1 polypeptide ligand (particularly an antibody) as specified herein. Such method may allow subsequent analysis of the sample with regard to its likelihood of being associated with a medical condition or a favourable outcome of a treatment as described herein, without making the actual step of medical analysis.

Wherever alternatives for single separable features such as, for example, a ligand type or medical indication are laid out herein as "embodiments", it is to be understood that such alternatives may be combined freely to form discrete embodiments of the invention disclosed herein. Thus, any of the alternative embodiments for a ligand type may be combined with any of the alternative embodiments of a medical indication mentioned herein.

The invention is further illustrated by the following examples and figures, from which further embodiments and advantages can be drawn. These examples are meant to illustrate the invention but not to limit its scope.

EXAMPLES

Example 1: ARTC1-Expression in Tumor Tissue Microarrays (TMA)

Tumor tissue overview array were obtained from the Pathology Department, University Hospital Zurich, and were stained for human ARTC1 by using a commercially available antibody that works on FFPE tissue (Abcam ab185293).

Cancers with positive ARTC1 staining are: breast, colon, lung, liver, glioma, kidney, testis, pancreas, sarcoma, melanoma, and prostate cancer.

A commercial multi cancer TMA (MC5003d from US Biomax) was stained for human ARTC1 by using a commercially available antibody that works on FFPE tissue (Abcam ab185293). Additional cancers with positive ARTC1 staining are: carcinomas of stomach, ovary, bladder, and uterus; melanoma, endometrioid adenocarcinoma, thyroid papillary carcinoma, cervix squamous carcinoma, Esophagus adenocarcinoma.

Figure 4:
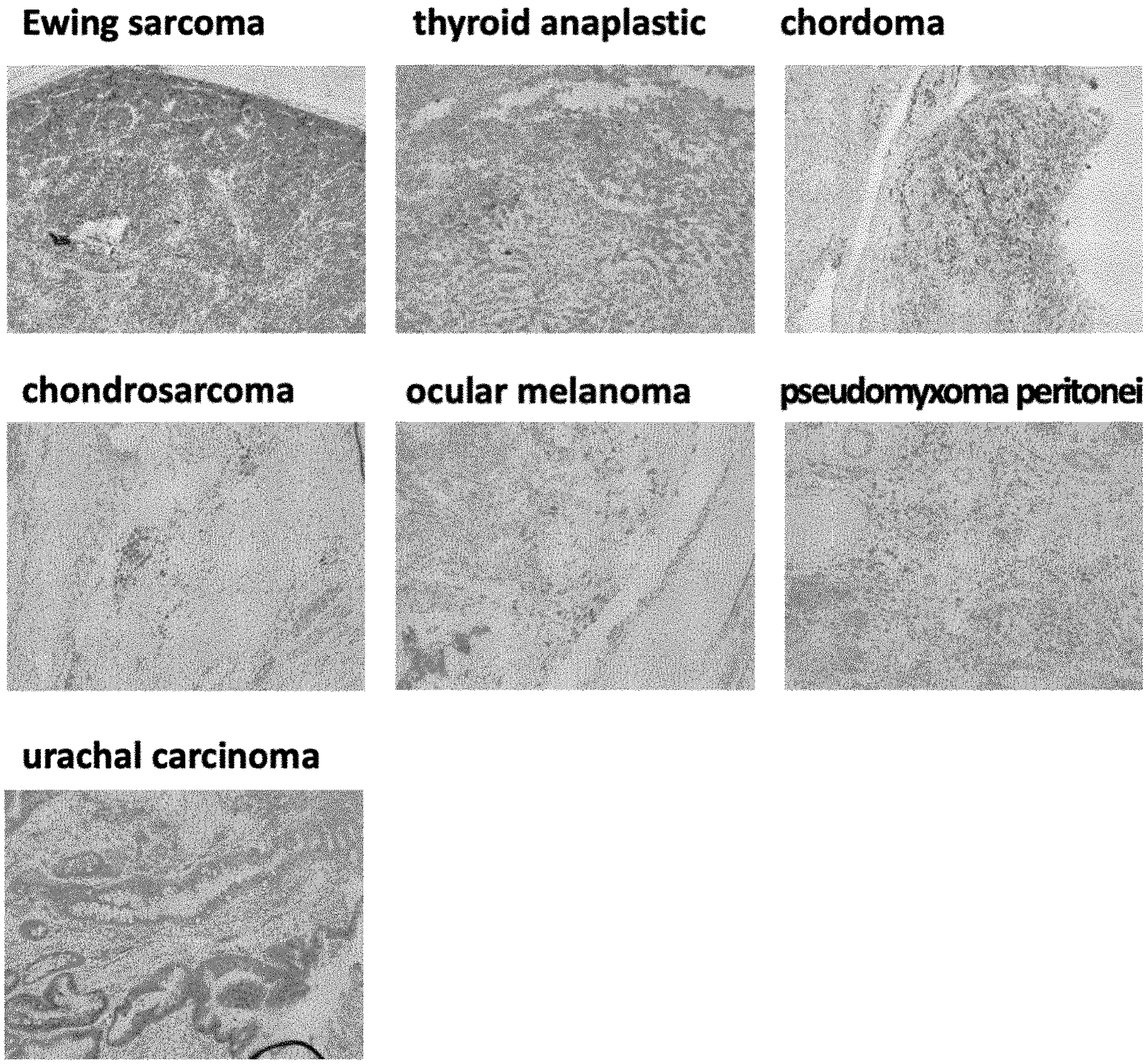
FIG. 4 shows sections from a collection of rare tumor types were stained for human ARTC1 (Abcam ab185293). All pictures were taken with a 10× objective.

Sections from rare tumor types (provided by a CRO and selected by an oncologist) were stained for human ARTC1 by using a commercially available antibody that works on FFPE tissue (Abcam ab185293). The following cancer types stained positive for ARTC1: Ewing sarcoma, thyroid anaplastic carcinoma, chordoma, chondrosarcoma, ocular melanoma, pseudomyxoma peritonei, and urachal carcinoma (FIG. 4).

Example 2: Correlation of Patient Data with ARTC1-Positivness 2.1 ARTC1-Expression Correlates with Reduced Survival.

Figure 1:
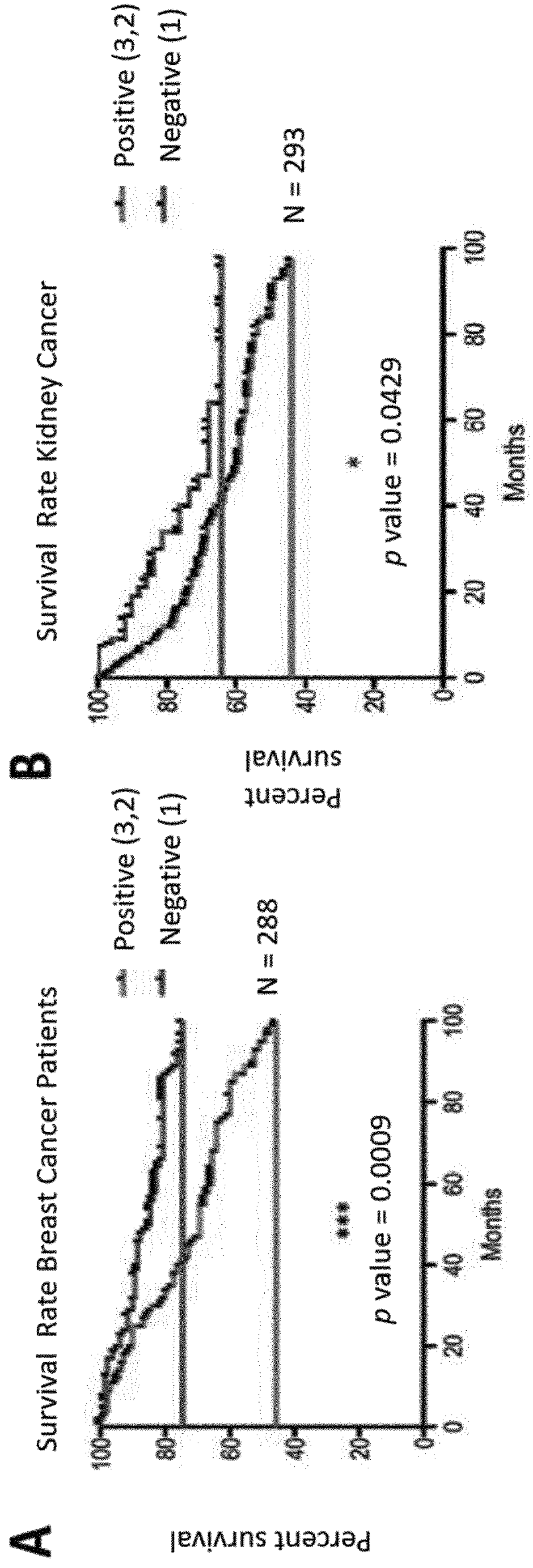
FIG. 1 shows that ARTC1-expression correlates with reduced survival of cancer patients. Organ-centric tumor TMAs were stained for human ARTC1. The staining was evaluated according to a 3 stage score (negative, weak and strong staining) and correlated with anonymous post-mortem patient data (weak and strong staining were combined as positive). Cases with bad tissue quality or missing patient data were omitted form the analysis. (A) Survival of breast cancer patients (all entities). (B) Survival of kidney cancer patients (all entities). (C) Survival of patients with lung adenocarcinoma. (D) Examples of stainings of individual tissue punches.
Figure 1:
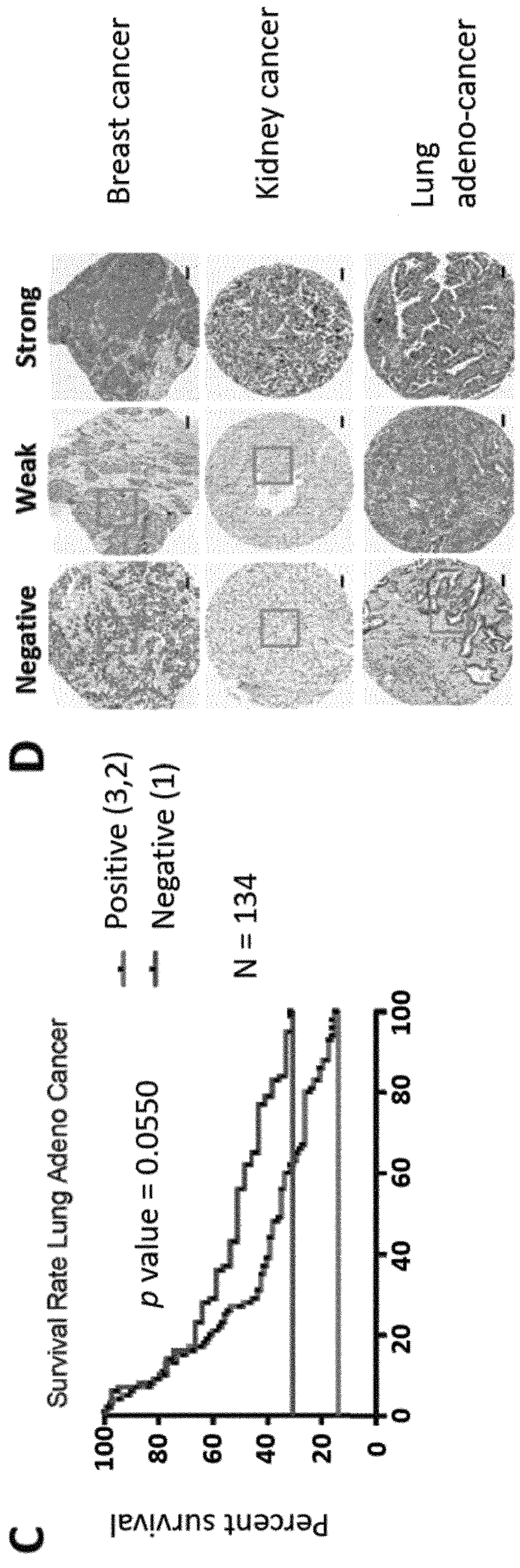

Organ-centric tumor TMAs were obtained from the Pathology Department, University Hospital Zurich, and were stained for human ARTC1 by using a commercially available antibody that works on FFPE tissue (Abcam ab185293). The ARTC1 staining was evaluated and correlated with anonymous post-mortem patient data. The analysis revealed that for all tumor types with sufficient patient data there is a negative correlation between ARTC1-expression and survival (FIG. 1).

2.2 ARTC1-Expression Correlates with More Severe Tumor Subtypes.

Figure 2:
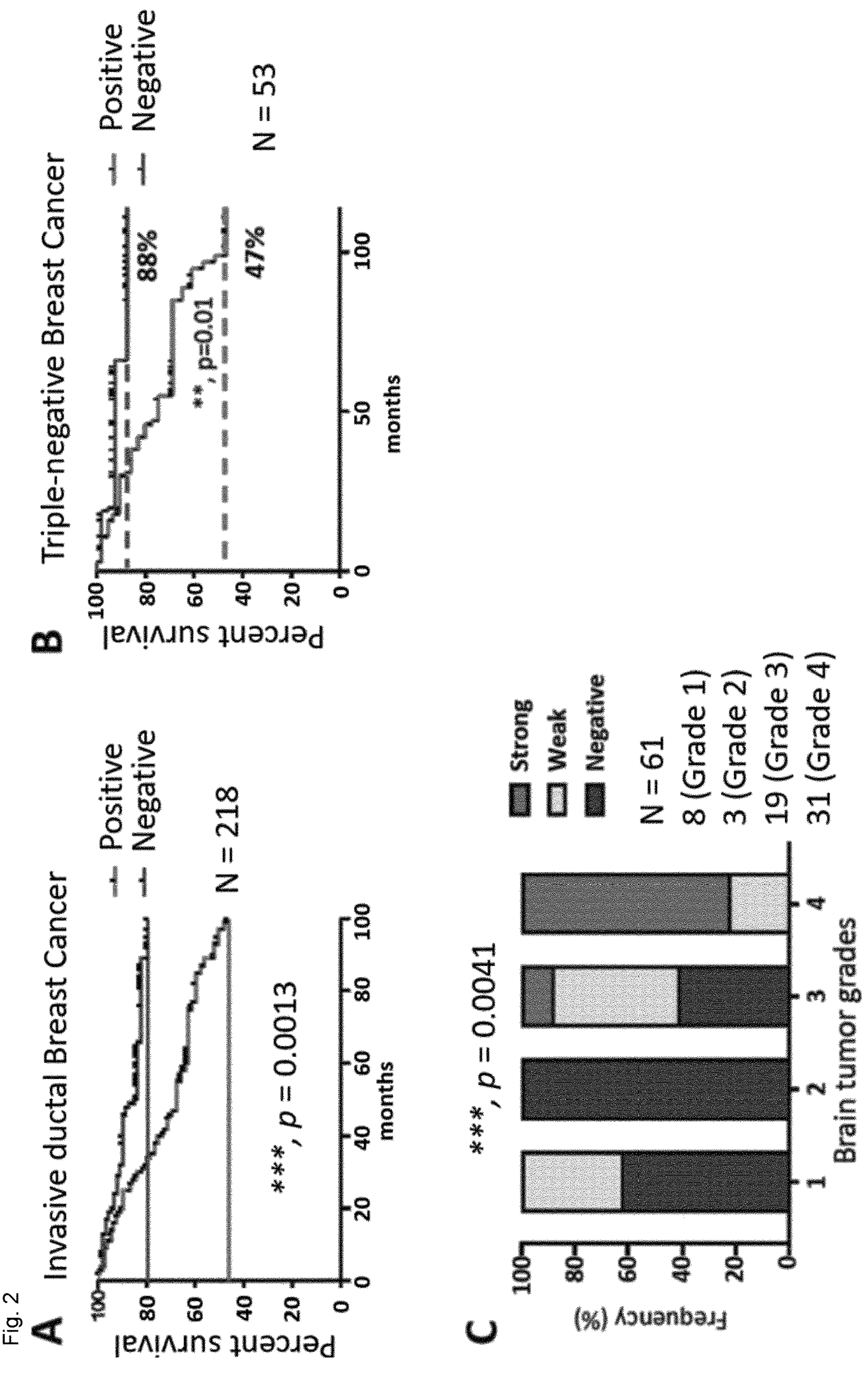
FIG. 2 shows that ARTC1-expression correlates with more severe subtypes of cancer. Tumor TMAs were stained and evaluated as explained in FIG. 1. (A) Correlation of survival and ARTC1-expression in patients with invasive ductal BrCa. (B) Correlation of survival and ARTC1-expression in patients with triple-negative BrCa, the most severe form of BrCa. (C) Correlation of ARTC1-expression and the tumor grade in patients with brain cancer.

The data from ARTC1-stained organ-centric TMAs were analysed for a correlation of ARTC1-expression with disease severity. Among the breast cancer cases, the negative correlation between ARTC1-expression and survival was clearly more pronounced among the more severe subtypes of breast cancer (BrCa): invasive ductal and triple-negative breast cancer (TNBC) (FIGS. 2A and B). The proportion of ARTC1-positive cases increases from ‘all BrCa’ over ‘invasive ductal BrCa’ until the most severe and currently least treatable form, the TNBC (48% vs 55% vs 74%, respectively). For TNBC, the difference in the 100-month survival expectancy is most pronounced among BrCa (88% for ARTC1-negative and 47% for ARTC1-positive cases). An analogous correlation between ARTC1-expression and tumor severity grade was observed for brain tumors (FIG. 2C). While low grade tumors (pilostystic astrocytoma (grade 1) and low-grade astrocytoma (grade 2) are nearly negative for ARTC1, anaplastic astrocytoma (grade 3) shows 60% mainly weak staining. In contrast, glioblastoma (grade 4) are 100% positive with 80% strong staining.

Example 3: Absence of ARTC1-Expression in Normal Tissue

Staining of normal control tissue TMAs (commercial and from Department of Pathology, University Hospital Zurich) reveals absence of ARTC1 expression in most normal tissues with the exception of very weak expression in skeletal and heart muscle (data not shown). These protein expression data confirm previous reports that were only based on RNA expression.

Example 4: Treatment Data

Figure 3:
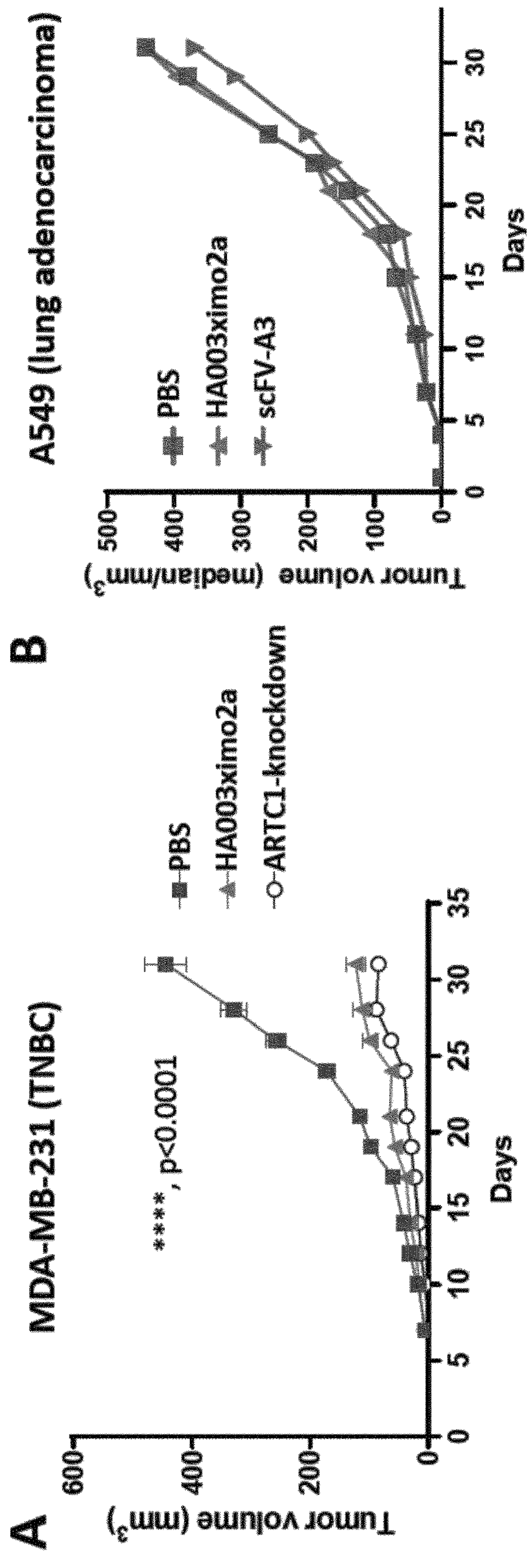
FIG. 3 shows treatment with an antibody blocking the enzymatic function of ARTC1. Human cancer cell lines were transduced with human ARTC1, with an empty vector (as control) or with an shRNA construct to knock down endogenous ARTC1 expression. (A) 0.5 Mio MDA-MB-231 cells were injected orthotopically into the mammary fat pads. Starting from day 7 after tumor inoculation, the treatment group received twice weekly by intraperitoneal injection 15 mg/kg of the enzyme-neutralizing anti-human ARTC1 antibody HA003ximo2a. The control group received vehicle (PBS) only. Tumor size was measured with a caliper. (B) 1 Mio A549 cells were injected s.c. into the flanks of CB17-Scid mice. Starting from day 7 after tumor inoculation, the treatment group received once weekly by intraperitoneal injection 3 mg/kg of the enzyme-neutralizing anti-human ARTC1 antibody HA003ximo2a or a scFv version of rat A3 fused to a rabbit IgG-Fc in a molar amount equivalent to 6.75 mg/kg of a full IgG antibody. (C) MDA-MB-231 (left) and A549 (right) transduced with either empty vector or with full-length human ARTC1 were grown in CB17-Scid mice.
Figure 3:
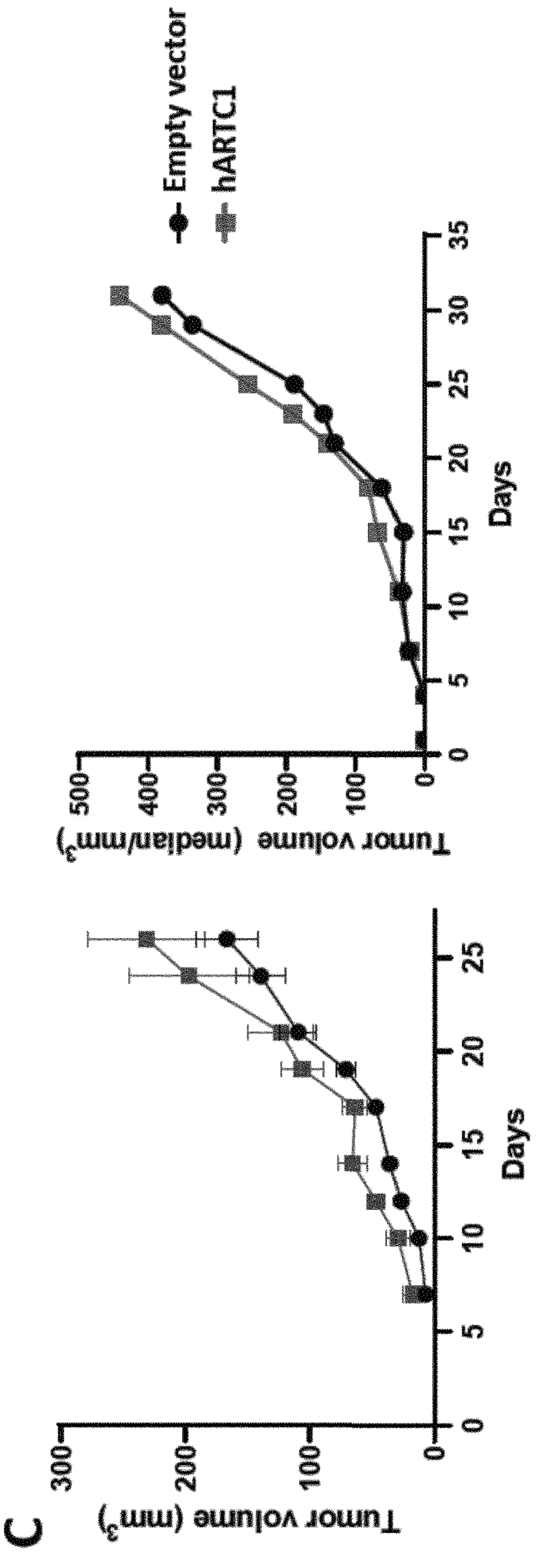

To show that ARTC1 is a therapeutic target in human cancers, the inventors established in vivo cancer models of human cancer cell lines grown in CB17-Scid mice. As for the moment, the inventors have not yet identified established cancer cell lines that express detectable ARTC1 at the cell surface in vitro, thus, they transduced cell lines with full length human ARTC1 or as control with an shRNA to knockdown endogenous ARTC1. The human TNBC cell line MDA-MB-231 (0.5 Mio) were injected orthotopically into the mammary fat pads. Starting from day 7 after tumor inoculation, the treatment group received twice weekly by intraperitoneal injection 15 mg/kg of the enzyme-neutralizing anti-human ARTC1 antibody HA003ximo2a (VH and VL domains of the original rat A3 clone were fused to murine IgG2a/K constant regions). The data shows that with an antibody treatment targeted to extracellular ARTC1, the tumor growth can be reduced as efficiently as with ARTC1 knock-down (FIG. 3A). This data shows that patients can be treated by a therapy targeted to ARTC1 either by an antibody, RNA interference or a small molecule inhibitor.

In another experimental setting, the inventors treated with twice weekly 5 mg/kg anti-human ARTC1 antibody HA003ximo2a and obtained a nearly as pronounced treatment effect as with 15 mg/kg (data not shown).

In another treatment experiment, human lung adenocarcinoma A549 cells (1 Mio) were injected s.c. into the flanks of CB17-Scid mice. Starting from day 7 after tumor inoculation, the treatment group received once weekly by intraperitoneal injection 3 mg/kg of the enzyme-neutralizing anti-human ARTC1 antibody HA003ximo2a (FIG. 3B). A second group received once weekly a scFv version of rat A3 fused to a rabbit IgG-Fc in a molar amount equivalent to 6.75 mg/kg of a full IgG antibody. The data shows that a treatment with 3 mg/kg antibody once weekly had no effect, while an equivalence dose of 6.75 mg/kg already slightly delayed tumor growth.

FIG. 3C shows that ectopic expression of human ARTC1 in human cancer cell lines leads to an enhanced tumor growth in CB17-Scid mice (FIG. 3C, left MDA-MB-231, right A549). Thus, FIG. 3A (knockdown) and FIG. 3C prove that ARTC1 is a drive of tumor growth.

Figure 5:
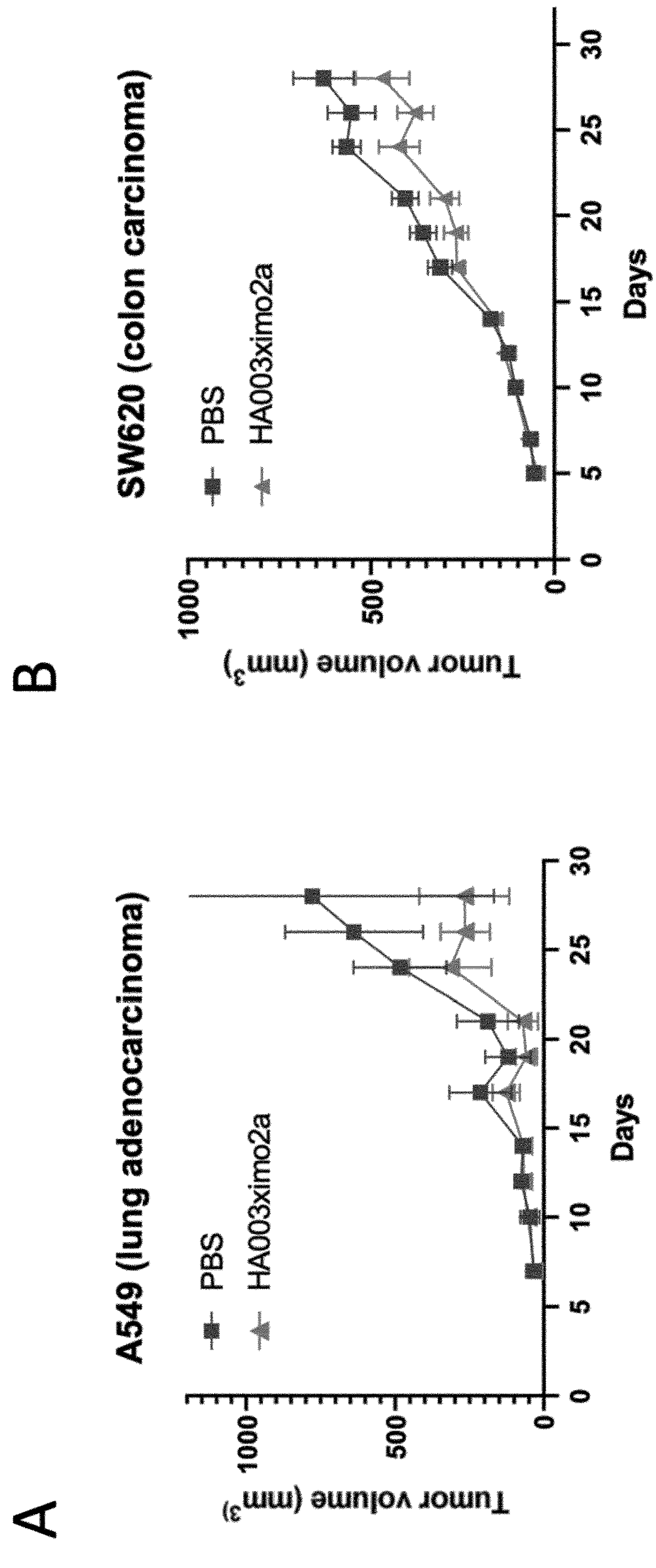
FIG. 5 shows (A) A549 (0.5 Mio) cells transduced to express human ARTC1 were inoculated subcutaneously into CB17-Scid animals and treated in the same scheme as in FIG. 3A. (B) SW620 (0.5 Mio) cells transduced to express human ARTC1 were inoculated subcutaneously into CB17-Scid animals and treated in the same scheme as in FIG. 3A. (C) The antibody clone A197 was recombinantly produced in the form of rat-mouse chimeric antibody and was named MA197ximo2a. 4T1 (10E4 cells) transduced to express mouse ARTC1 (mARTC1) were inoculated subcutaneously into BALB/c animals and treated in the same scheme as in FIG. 3A but with antibody MA197ximo2a. (D) MC38 murine colon carcinoma cells were either control transduced (EV) or transduced with mARTC1. For the experimental metastasis model, 0.3 Mio cells were injected intravenously and the animal's lung weights were determined after 3 weeks.
Figure 5:
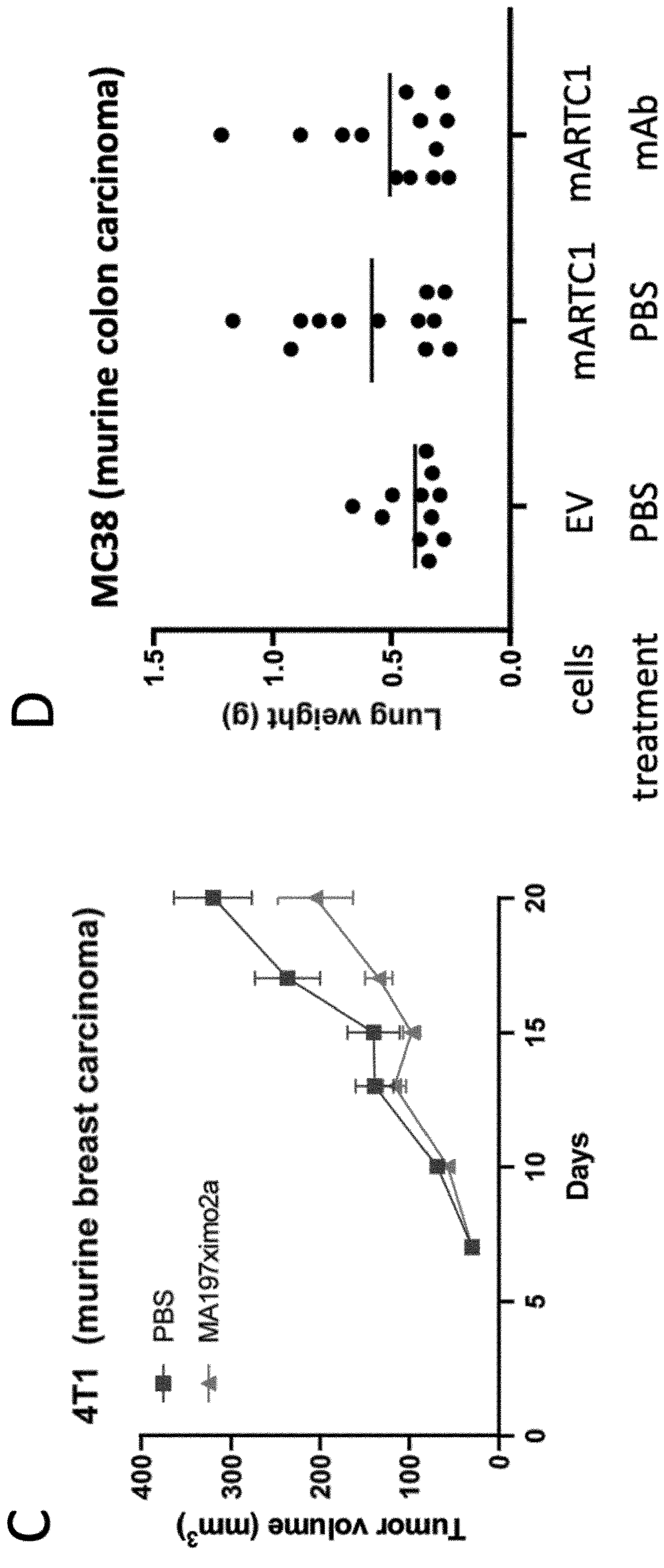

In another treatment experiment, human A549 lung or SW620 colon carcinoma cells, respectively, were injected subcutaneously in CB17-Scid mice and animals were treated from day 7 on with 15 mg/kg HA003ximo2a i.p. twice weekly (FIGS. 5A and 5B).

In another treatment experiment, murine syngeneic 4T1 breast cancer cells were injected orthotopically into BALB/c mice and animals were treated from day 7 on with 15 mg/kg MA197ximo2a i.p. twice weekly (FIG. 5C). The results show that the ARTC1-targeted treatment also works in a fully syngeneic system and in the presence of a full immune system.

In another treatment experiment, murine syngeneic MC38 colon carcinoma cells were injected i.v. in wildtype C57BL/6 animals and animals were treated from day 0 on with 15 mg/kg MA197ximo2a i.p. twice weekly (FIG. 5D). Lungs were harvested on day 21 and treated with Bouin's solution. Metastases nodules (not shown) and lung weights were determined. These experiments revealed that ARTC1 contributes to disease severity by enhancing metastatic seeding. Antibody treatment led to a reduction of metastatic burden.

Example 5: MOA

The mechanism of action is twofold: 1. by inhibition of ADP-ribosylation (ADPR), and 2. via antibody-dependent cellular cytotoxicity (ADCC).

Evidence for a role of inhibition of ADPR via blockade of ARTC1 by the therapeutic antibody comes from mass spectrometry analyses of ADP-ribosylation in human tumor cells and samples of solid tumors derived from the above described experimental treatment models (MDA-MB-231 (TNBC) and A549 (LuCa)). The inventors identified ADP-ribosylated proteins that are involved in tumor growth (growth factor and receptors), vascularization, metastasis and immune regulation (cytokines and their receptors).

Furthermore, upon antibody treatment or shRNA knockdown, these proteins are not ADP-ribosylated anymore.

Figure 6:
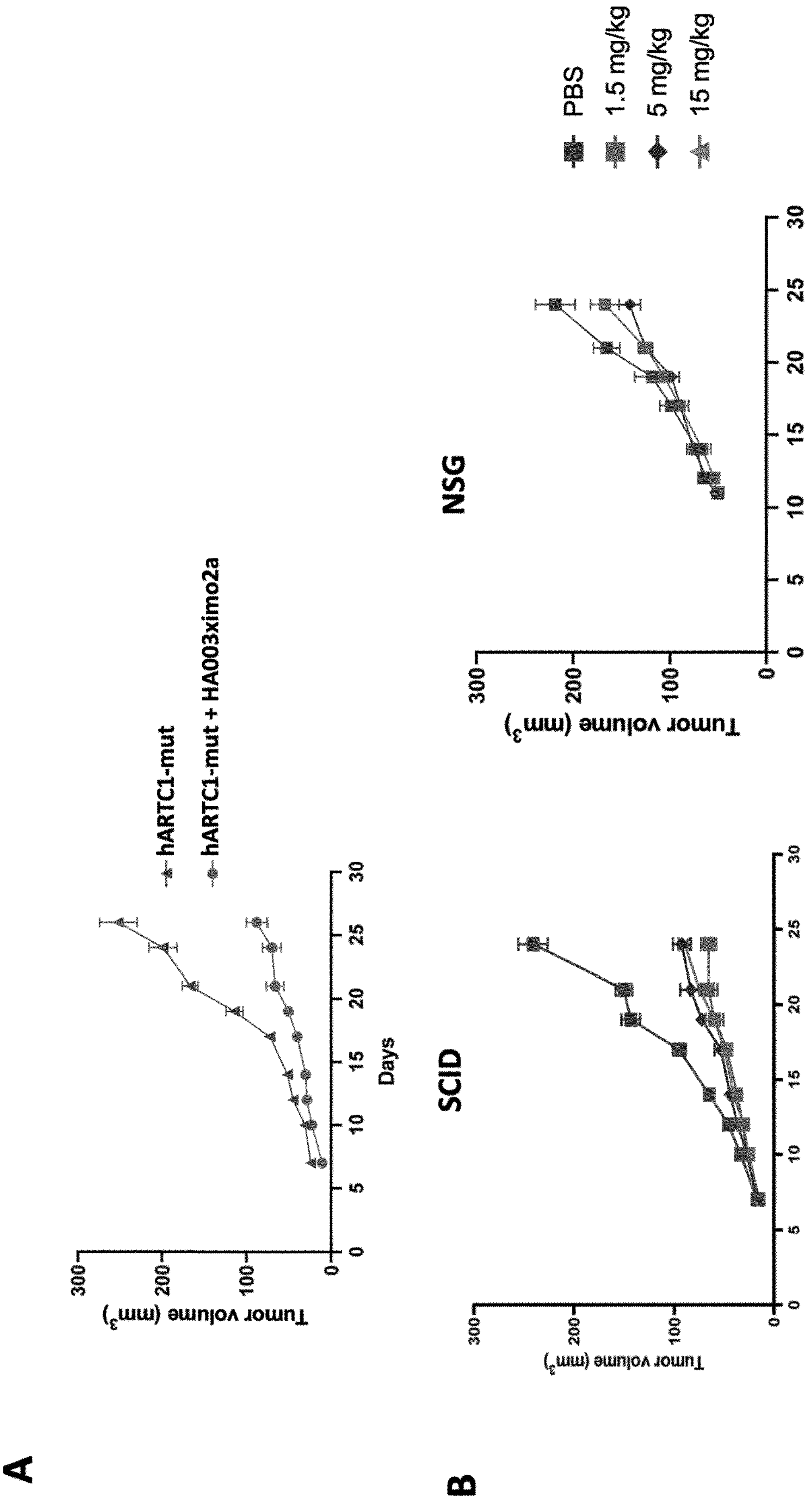
FIG. 6 shows (A) MDA-MB-231 cells were transduced with enzymatically inactive mutant human ARTC1 (hARTC1-mut) and were inoculated orthotopically into CB17-Scid animals. Treatment was as in FIG. 3A. (B) Human ARTC1-expressing MDA-MB-231 cells were inoculated into CB17-Scid or NOD-Scid-γc (NSG) animals and the animals were treated twice weekly with the indicated doses. (C) MDA-MB-231 cells which were either control transduced (EV), knockdown for ARTC1 (KD) or overexpress ARTC1 (OE) were grown and treated as in FIG. 3A. At the end of the experiment, tumors were prepared for mass spectrometric analysis of ADP-ribosyl modifications. The graph shows the number of unique arginine ADP-ribosylation sites. (D) Tumors from the same experiment as in 6C were prepared for histological analysis. Sections were stained with the Af1521-Fc reagent. (E) Human ARTC1-expressing MDA-MB-231 cells were inoculated into CB17-Scid and the animals were treated as in FIG. 3A (PBS or HA003ximo2a). At the end of the experiment, tumors were prepared for histology and section were stained for the indicated markers. (F) Section of the same samples as in 6D were stained for CD31 and the area of DAB staining was measured with Fiji software.
Figure 6:
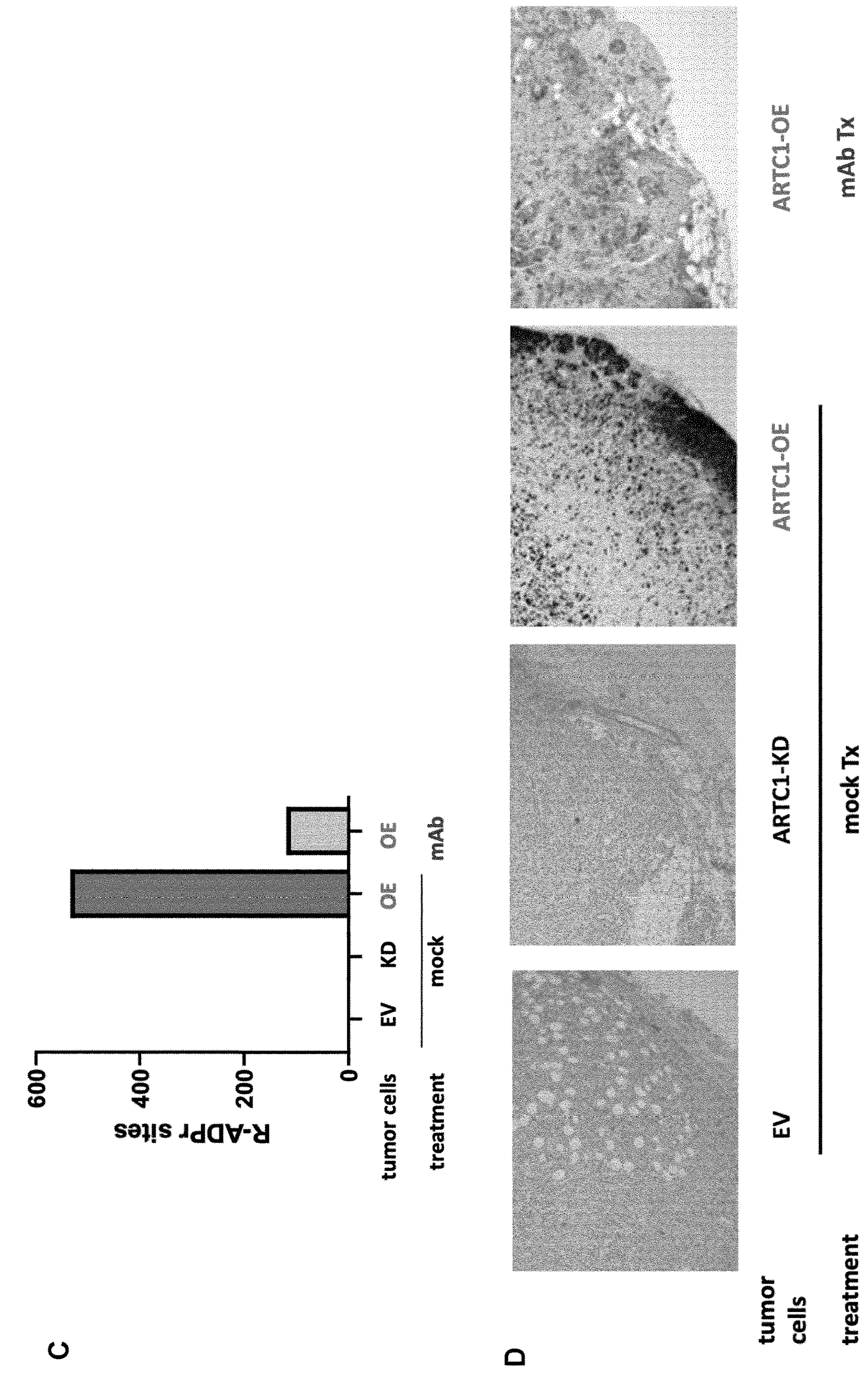
Figure 6:
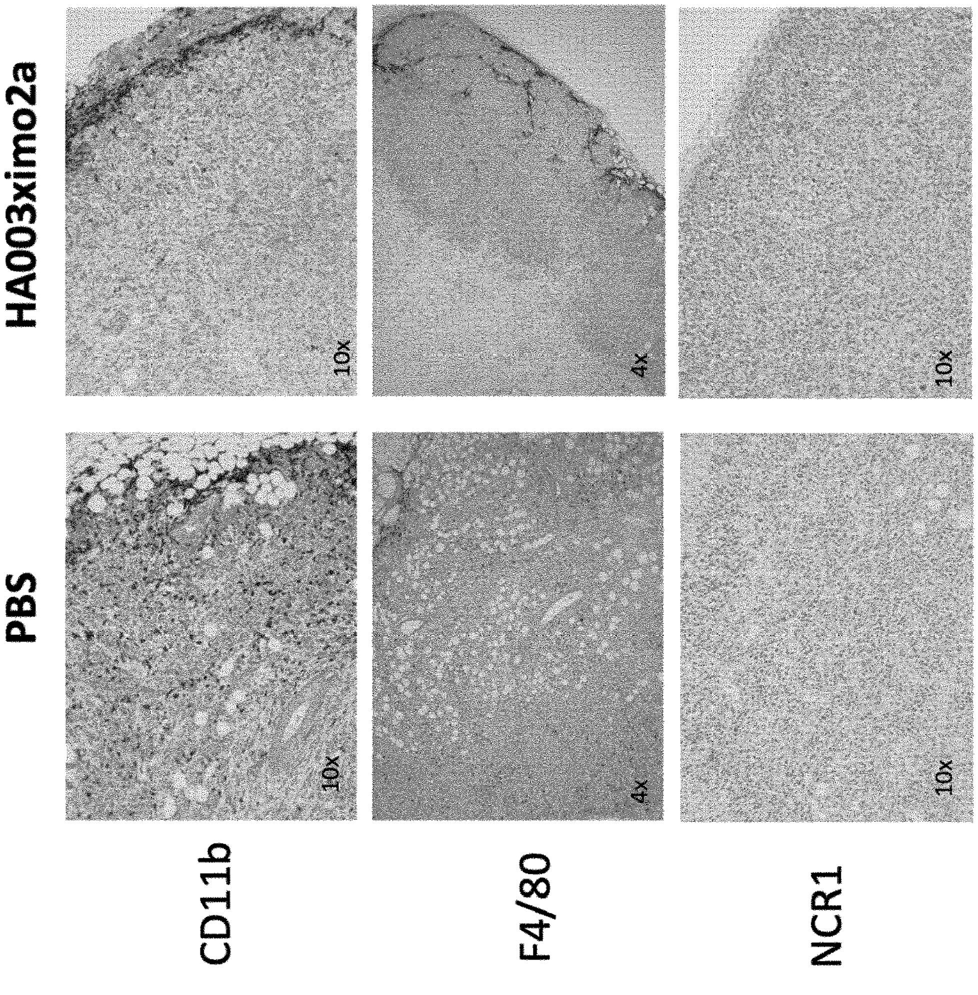
Figure 6:
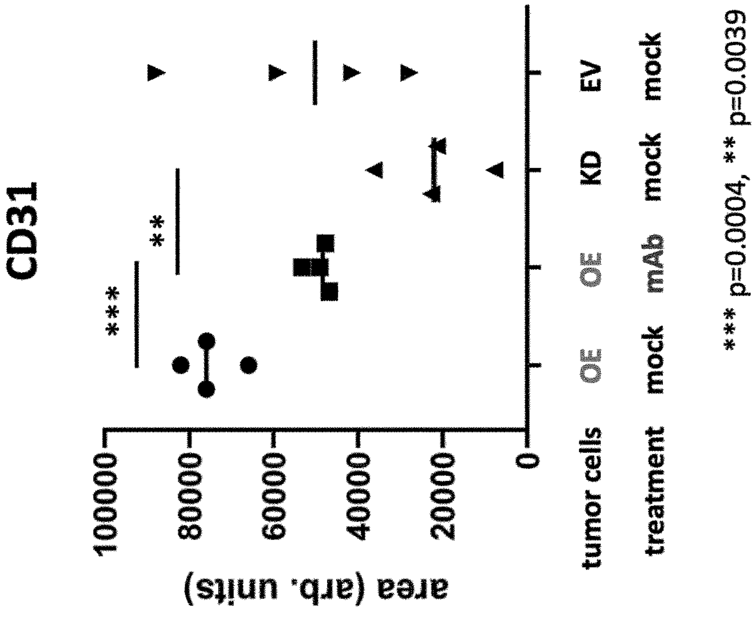

Evidence for a role of ADCC in the MOA of the antibody therapy comes from the experiment in which MDA-MB-231 cells expressing an enzymatically inactive form of human ARTC1 (FIG. 6A, hARTC1-mut). The experiment shows that a very efficient treatment effect can be achieved, without the need to block the enzymatic function. The ADCC mediated by the mouse IgG2a Fc part of the HA003ximo2a antibody is sufficient for a treatment effect in this experimental setting. The results show that the tumor growth can be reduced also if the inhibitory function of the antibody is irrelevant, indicating that NK cell and macrophage-mediated cellular are also engaged by the antibody.

In another treatment experiment, the inventors compared the efficacy of treating ARTC1-expressing MDA-MB-231 cells inoculated either in CB17-Scid or NOD-Scid-γc (NSG) mice and treated the animals with different doses of HA003ximo2a twice weekly starting from day 7 (FIG. 6B). The results indicate that the antibody treatment has an effect even in the complete absence of immune cells, while the ARTC1-inhibitory capacity is retained in this system.

To determine the extent of enzyme inhibition in vivo upon antibody treatment, the inventors isolated treated and untreated MDA-MB-231 tumors from treatment experiments in CB17-Scid mice and analyzed the ADP-ribosylome using published mass spectrometry methods (Nowak et al., *Nat Commun* 11(1):5199). The analysis shows that while in parental (WT) or ARTC1-knockdown (KD) MDA-MB-231 tumors, only very few Arginine-specific ADP-ribosylation (R-ADPr) sites could be detected, a large number of peptides modified at R-ADPr sites were detected in ARTC1 overexpressing (OE) MDA-MB-231 cells and that the number of detected sites is strongly reduced upon antibody treatment (FIG. 6C). The reduced extent of ADP-ribosylation was furthermore confirmed by staining histological section of the respective tumors with the Af1521-Fc reagent which binds ADP-ribose and can be visualized by anti-Fc staining. The histological data confirm the mass spectrometry data as a strongly reduced ADP-ribosylation staining was obtained in anti-ARTC1 treated tumors (FIG. 6D).

Histological analysis of treated and untreated MDA-MB-231 tumors from treatment experiments in CB17-Scid mice revealed an influence on immune cell infiltration (FIG. 6E). CD11 b is present on all myeloid cells including the myeloid derived suppressor cells (M DSC) which are frequently populating immunologically cold tumors. CD11b+ cells could be detected throughout the ARTC1-expressing control tumors while CD11b+ cells were confined to the tumor borders in antibody-treated tumors. F4/80 is expressed by macrophages and could be detected at a moderate frequency within control tumors. In contrast, strong vessel-associated F4/80 staining was detected in antibody-treated tumors. The natural killer cell receptor NCR1/NKp46 characterizes NK cells. While hardly any NK cells could be detected in control tumors, a strongly enhanced NK cell infiltration was detectable in antibody-treated tumors although with a low signal intensity. The inventors had identified ARTC1-dependent ADP-ribosylation marks also on molecules of the vascularization pathway (data not shown). To determine whether tumor vascularization was affected by anti-ARTC1 antibody treatment, histological section of treated and untreated MDA-MB-231 tumors from treatment experiments in CB17-Scid mice were stained for PECAM-1/CD31 which is expressed on early and mature endothelial cells. Human ARTC1-expressing tumor contained the highest amount of CD31 staining suggesting that ARTC1 activity promotes neovascularization within tumors. Antibody treatment or knockdown of ARTC1 was associated with reduced CD31 staining, suggesting that reduced tumor growth is in part due to reduced neovascularization owing to reduced or absent ARTC1 activity (FIG. 6F).

Figure 7:
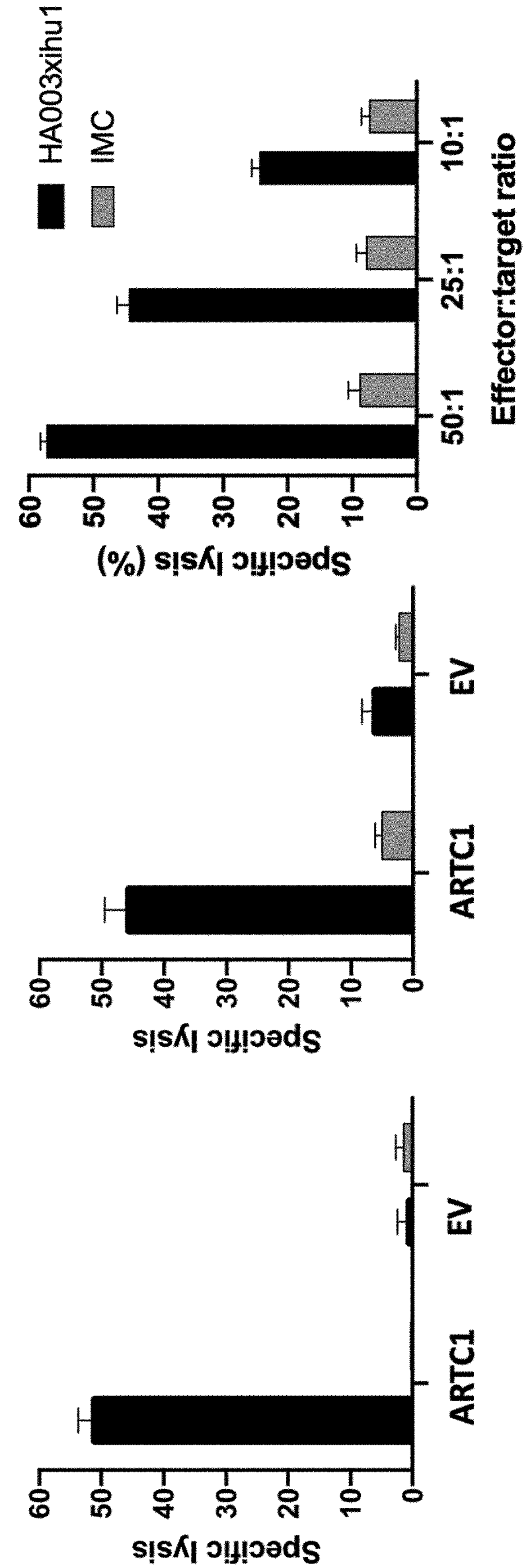
FIG. 7 shows that antibody-dependent cellular cytotoxicity (ADCC) assays were performed with PBMCs from three different donors either at a fixed effector:target ratio of 50:1 or at titrating ratios. A549 that were either control transduced (EV) or transduced with human ARTC1 served as targets. A human IgG1 Fc chimeric form of HA003 or an isotype-matched control (IMC) was used at 10 ug/ml.

To confirm that indeed anti-ARTC1 antibodies can mediate antibody-dependent cellular cytotoxicity (ADCC), the authors performed in vitro ADCC assays with human PBMC as effector cells. The data shows that the presence of ARTC1 on MDA-MB-231 cells allows the antibody HA003ximo2a (10 μg/mL) to induce strong ADCC at an effector:target ratio of 50:1 (FIG. 7, left and middle, two donors). Furthermore, the data shows that the ADCC is also effector cell dependent (FIG. 7 right).

Example 6: Safety Data

Figure 8:
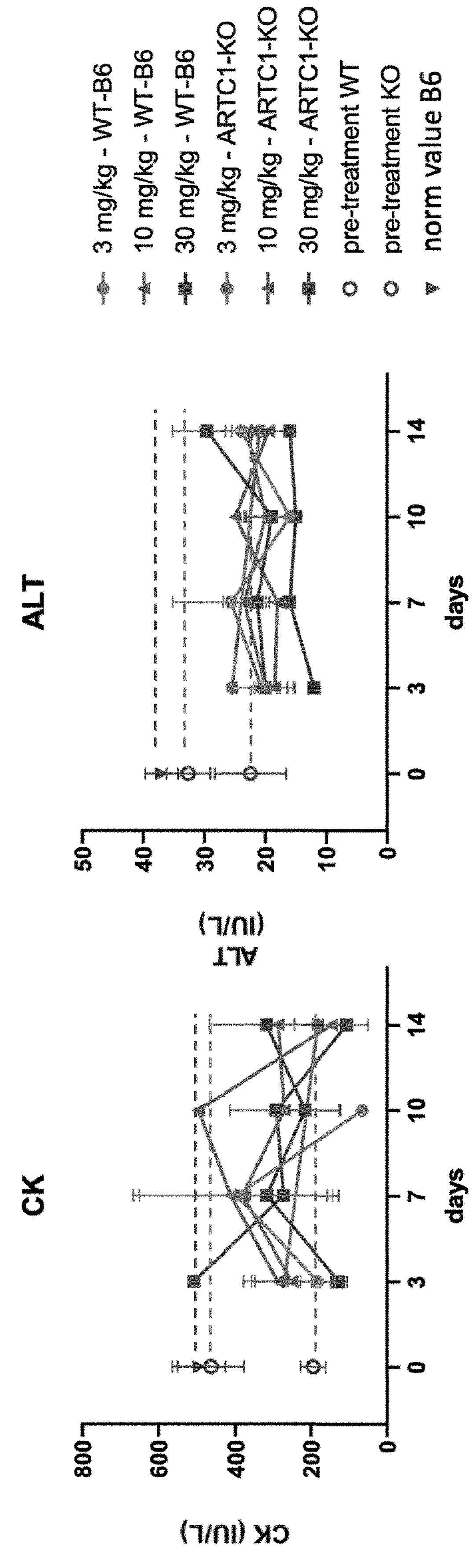
FIG. 8 shows that wildtype C57BL/6 (WT-B6) or ARTC1-deficient (ARTC1-KO) animals were injected with a single dose of MA197ximo2a at day 0 i.p. and were bled on the indicated days. Blood plasma was analysed for creatine kinase (CK) and alanine aminotransferase (ALT).

A preliminary safety evaluation was performed by injection of different doses of anti-mouse ARTC1 antibody MA197ximo2a into naïve wildtype C57BL/6 animals or ARTC1-deficient mice. Blood plasma was sampled at days 3, 7, 10 and 14 and the levels of creatine kinase (CK) and alanine aminotransferase (ALT) were determined on a Beckman-Coulter SYNCHRON DxC800 system as measures of muscle and liver toxicity, respectively. No antibody-dependent toxicity was observed in neither of the doses. The blood CK and ALT levels in treated C57BL/6 animals were not elevated and were comparable both to treated ARTC1-deficient animals (in which no target engagement can occur) and normal C57Bl/6 values from the literature (*Mamm Genome* 15:768) (FIG. 8).

Amino Acid Sequence of Human ARTC1

The amino acid sequence of human ARTC1 (hARTC1) is provided in the Uniprot database (www.uniprot.org) under identifier P52961.

hARTC1 (SEQ ID NO 001):
MQMPAMMSLLLVSVGLMEALQAQSHPITRRDLFS

QEIQLDMALASFDDQYAGCAAAMTAALPDLNHTE

FQANQVYADSWTLASSQWQERQARWPEWSLSPTR

PSPPPLGFRDEHGVALLAYTANSPLHKEFNAAVR

EAGRSRAHYLHHFSFKTLHFLLTEALQLLGSGQR

PPRCHQVFRGVHGLRFRPAGPRATVRLGGFASAS

LKHVAAQQFGEDTFFGIWTCLGAPIKGYSFFPGE

EEVLIPPFETFQVINASRLAQGPARIYLRALGKH

STYNCEYIKDKKCKSGPCHLDNSAMGQSPLSAVW

SLLLLLWFLVVRAFPDGPGLL

The human ARTC1 comprises an NAD+-binding catalytic site that is characterized by the catalytic triad RSE built by the three amino acids Arg179, Ser202 and Glu238 of SEQ ID NO 001.

hARTC1 [160-200] SEQ ID NO 002:
EALQLLGSGQRPPRCHQVFRGVHGLRFRPAGPRATVRLGGF hARTCI [180-220] SEQ ID NO 003:
GVHGLRFRPAGPRATVRLGGFASASLKHVAAQQFGEDTFFG hARTCI [220-260] SEQ ID NO 004:
GIWTCLGAPIKGYSFFPGEEEVLIPPFETFQVINASRLAQG

TABLE 1

Rat antibodies used in this study

| Antibody | SEQ ID NO | type |
|---|---|---|
| RG4-A111 | 005 | Heavy chain |
| | 006 | Light chain |
| | 007 | recombinant scFV |
| R19-A3 | 008 | Heavy chain |
| | 009 | Light chain |
| | 010 | recombinant scFV |
| R17254-A271 | 011 | Heavy chain |
| | 012 | Light chain |
| | 013 | recombinant scFV |
| R17254-A327 | 014 | Heavy chain |
| | 015 | Light chain |
| | 016 | recombinant scFV |
| R17254-A197 | 017 | Heavy chain |
| | 018 | Light chain |
| | 019 | recombinant scFV |

TABLE 2

CDR sequences

| KABAT | LCDR1 (SEQ ID NO) | LCDR2 (SEQ ID NO) | LCDR3 (SEQ ID NO) |
|---|---|---|---|
| RG4-A111 | RASSSVSYMY (020) | ETSKLAS (025) | QQWNYPSCT (030) |
| R19-A3 | RASSGVSYMA (021) | GTSKLAS (026) | QQCCSTPLT (031) |
| A271 | KSSQSLLSSG NQKNYLA( 022) | YASTRQS (027) | LQHYISPFT (032) |
| A327 | KTSQNVDYYG ITYMH (023) | EGSNLPS (028) | QQSKDYPWT (033) |
| A197 | RASSSVSYMY (024) | DTSKLAS (029) | QQWSSSPSMT (034) |
| **KABAT** | **LCDR2 long(SEQ ID NO)** | | |
| RG4-A111 | ETSKLASGVPD (050) | | |
| R19-A3 | GTSKLASGVPN (051) | | |
| A271 | YASTRQSGVPD (052) | | |
| A327 | EGSNLPSGIPA (053) | | |
| A197 | DTSKLASGVPN (054) | | |
| **KABAT** | **HCDR1 (SEQ ID NO)** | **HCDR2 (SEQ ID NO)** | **HCDR3 (SEQ ID NO)** |
| RG4-A111 | NFAMA (035) | SISYDGVN TYYRD (040) | RGAAPFDF (045) |
| R19-A3 | DYAMV (036) | TITYDGSR IYYRD (041) | QGGYTTDY YYVMDA (046) |
| A271 | DFPMA (037) | TISTGGGTT YYRG (042) | PLYYSNYV GNVMDA (047) |
| A327 | INYWD (038) | HINYSGGT NYNP (043) | EGAGGLDY (048) |
| A197 | NFPMA (039) | WSISGGAT YYRD (044) | GDGSSRGYYFDY (049) |
| **KABAT** | **HCDR2 long (SEQ ID NO)** | | |
| RG4-A111 | SISYDGVNTYYRDSVRG (055) | | |
| R19-A3 | TITYDGSRIYYRDSVRG (056) | | |
| A271 | TISTGGGTTYYRGSVRG (057) | | |
| A327 | HINYSGGTNYNPSLRS (058) | | |
| A197 | WSISGGATYYRDSVRG (059) | | |

The invention claimed is:

1. A method for treating a cancer expressing ARTC1, comprising:

administering to a subject in need thereof a non-agonist antibody or antibody-like molecule of ARTC1, thereby treating the cancer expressing ARTC1 wherein said antibody or antibody-like molecule binds to ARTC1 and inhibits the ADP-ribosyltransferase activity of ARTC1, wherein said antibody or antibody-like molecule comprises a light chain variable region comprising LCDR1, LCDR2 and LCDR3 and a heavy chain variable region comprising HCDR1, HCDR2 and HCDR3 and wherein a. LCDR1 is a CDR1 comprised in a sequence selected from SEQ ID NO 006, SEQ ID NO 009, SEQ ID NO 012, SEQ ID NO 015 and SEQ ID NO 018;

b. LCDR2 is a CDR2 comprised in a sequence selected from SEQ ID NO 006, SEQ ID NO 009, SEQ ID NO 012, SEQ ID NO 015 and SEQ ID NO 018;

c. LCDR3 is a CDR3 comprised in a sequence selected from SEQ ID NO 006, SEQ ID NO 009, SEQ ID NO 012, SEQ ID NO 015 and SEQ ID NO 018;

d. HCDR1 is a CDR1 comprised in a sequence selected from SEQ ID NO 005, SEQ ID NO 008, SEQ ID NO 011, SEQ ID NO 014 and SEQ ID NO 017;

e. HCDR2 is a CDR2 comprised in a sequence selected from SEQ ID NO 005, SEQ ID NO 008, SEQ ID NO 011, SEQ ID NO 014 and SEQ ID NO 017; and f. HCDR3 is a CDR3 comprised in a sequence selected from SEQ ID NO 005, SEQ ID NO 008, SEQ ID NO 011, SEQ ID NO 014 and SEQ ID NO 017.

2. The method of claim 1, wherein said antibody or said antibody-like molecule comprises a light chain variable region comprising LCDR1, LCDR2 and LCDR3 and a heavy chain variable region comprising HCDR1, HCDR2 and HCDR3 and wherein a. said LCDR1 is identical to an LCDR1 reference sequence selected from SEQ ID NO 020, SEQ ID NO 021, SEQ ID NO 022, SEQ ID NO 023 and SEQ ID NO 024;
b. said LCDR2 is identical to an LCDR2 reference sequence selected from SEQ ID NO 025, SEQ ID NO 026, SEQ ID NO 027, SEQ ID NO 028 and SEQ ID NO 029;
c. said LCDR3 is identical to an LCDR3 reference sequence selected from SEQ ID NO 030, SEQ ID NO 031, SEQ ID NO 032, SEQ ID NO 033 and SEQ ID NO 034;
d. said HCDR1 is identical to a HCDR1 reference sequence selected from SEQ ID NO 035, SEQ ID NO 036, SEQ ID NO 037, SEQ ID NO 038 and SEQ ID NO 039;
e. said HCDR2 is identical to a HCDR2 reference sequence selected from SEQ ID NO 040, SEQ ID NO 041, SEQ ID NO 042, SEQ ID NO 043 and SEQ ID NO 044; and
f. said HCDR3 is identical to a HCDR3 reference sequence selected from SEQ ID NO 045, SEQ ID NO 046, SEQ ID NO 047, SEQ ID NO 048 and SEQ ID NO 049.

3. The method of claim 1, wherein a. said LCDR1 is selected from SEQ ID NO 020, SEQ ID NO 021, SEQ ID NO 022, SEQ ID NO 023 and SEQ ID NO 024;
b. said LCDR2 is selected from SEQ ID NO 025, SEQ ID NO 026, SEQ ID NO 027, SEQ ID NO 028 and SEQ ID NO 029;
c. said LCDR3 is selected from SEQ ID NO 030, SEQ ID NO 031, SEQ ID NO 032, SEQ ID NO 033 and SEQ ID NO 034;
d. said HCDR1 is selected from SEQ ID NO 035, SEQ ID NO 036, SEQ ID NO 037, SEQ ID NO 038 and SEQ ID NO 039;
e. said HCDR2 is selected from SEQ ID NO 040, SEQ ID NO 041, SEQ ID NO 042, SEQ ID NO 043 and SEQ ID NO 044; and
f. said HCDR3 is selected from SEQ ID NO 045, SEQ ID NO 046, SEQ ID NO 047, SEQ ID NO 048 and SEQ ID NO 049.

4. The method of claim 1, wherein said antibody or said antibody-like molecule comprises a. said LCDR1 consisting of sequence SEQ ID NO 020, said LCDR2 consisting of sequence SEQ ID NO 025 or SEQ ID NO 050, said LCDR3 consisting of sequence SEQ ID NO 030, said HCDR1 consisting of sequence SEQ ID NO 035, said HCDR2 consisting of sequence SEQ ID NO 040 or SEQ ID NO 055, and said HCDR3 consisting of sequence SEQ ID NO 045,
b. said LCDR1 consisting of sequence SEQ ID NO 021, said LCDR2 consisting of sequence SEQ ID NO 026 or SEQ ID NO 051, said LCDR3 consisting of sequence SEQ ID NO 031, said HCDR1 consisting of sequence SEQ ID NO 036, said HCDR2 consisting of sequence SEQ ID NO 041 or SEQ ID NO 056, and said HCDR3 consisting of sequence SEQ ID NO 046,
c. said LCDR1 consisting of sequence SEQ ID NO 022, said LCDR2 consisting of sequence SEQ ID NO 027 or SEQ ID NO 052, said LCDR3 consisting of sequence SEQ ID NO 032, said HCDR1 consisting of sequence SEQ ID NO 037, said HCDR2 consisting of sequence SEQ ID NO 042 or SEQ ID NO 057, and said HCDR3 consisting of sequence SEQ ID NO 047,
d. said LCDR1 consisting of sequence SEQ ID NO 023, said LCDR2 consisting of sequence SEQ ID NO 028 or SEQ ID NO 053, said LCDR3 consisting of sequence SEQ ID NO 033, said HCDR1 consisting of sequence SEQ ID NO 038, said HCDR2 consisting of sequence SEQ ID NO 043 or SEQ ID NO 058, and said HCDR3 consisting of sequence SEQ ID NO 048, or
e. said LCDR1 consisting of sequence SEQ ID NO 024, said LCDR2 consisting of sequence SEQ ID NO 029 or SEQ ID NO 054, said LCDR3 consisting of sequence SEQ ID NO 034, said HCDR1 consisting of sequence SEQ ID NO 039, said HCDR2 consisting of sequence SEQ ID NO 044 or SEQ ID NO 059, and said HCDR3 consisting of sequence SEQ ID NO 049.

5. The method of claim 1, wherein said antibody or said antibody-like molecule comprises a. a first sequence at least 90% identical to one of SEQ ID NO 006, SEQ ID NO 009, SEQ ID NO 012, SEQ ID NO 015 and SEQ ID NO 018; and
b. a second sequence at least 90% identical to one of SEQ ID NO 005, SEQ ID NO 008, SEQ ID NO 011, SEQ ID NO 014 and SEQ ID NO 017.

6. The method of claim 1, wherein said antibody or said antibody-like molecule comprising a sequence at least 90% identical to one of SEQ ID NO 007, SEQ ID NO 010, SEQ ID NO 013, SEQ ID NO 016 and SEQ ID NO 019.

7. The method of claim 1, characterized in being able to prevent ADP-ribosylation of RR, RG, GR, RXR and GXXXXR motifs.

8. The method of claim 1, characterized in that said antibody or said antibody-like molecule is specifically reactive against a polypeptide encoded by any one of SEQ 001, SEQ 002, SEQ 003 or SEQ 004.

* * * * *

SEQUENCE LISTING

<160> NUMBER OF SEQ ID NOS: 59

<210> SEQ ID NO 1
<211> LENGTH: 327
<212> TYPE: PRT
<213> ORGANISM: Homo sapiens

<400> SEQUENCE: 1

```
Met Gln Met Pro Ala Met Met Ser Leu Leu Leu Val Ser Val Gly Leu
1               5                   10                  15

Met Glu Ala Leu Gln Ala Gln Ser His Pro Ile Thr Arg Arg Asp Leu
            20                  25                  30

Phe Ser Gln Glu Ile Gln Leu Asp Met Ala Leu Ala Ser Phe Asp Asp
        35                  40                  45

Gln Tyr Ala Gly Cys Ala Ala Ala Met Thr Ala Ala Leu Pro Asp Leu
    50                  55                  60

Asn His Thr Glu Phe Gln Ala Asn Gln Val Tyr Ala Asp Ser Trp Thr
65                  70                  75                  80

Leu Ala Ser Ser Gln Trp Gln Glu Arg Gln Ala Arg Trp Pro Glu Trp
                85                  90                  95

Ser Leu Ser Pro Thr Arg Pro Ser Pro Pro Pro Leu Gly Phe Arg Asp
            100                 105                 110

Glu His Gly Val Ala Leu Leu Ala Tyr Thr Ala Asn Ser Pro Leu His
        115                 120                 125

Lys Glu Phe Asn Ala Ala Val Arg Glu Ala Gly Arg Ser Arg Ala His
    130                 135                 140

Tyr Leu His His Phe Ser Phe Lys Thr Leu His Phe Leu Leu Thr Glu
145                 150                 155                 160

Ala Leu Gln Leu Leu Gly Ser Gly Gln Arg Pro Pro Arg Cys His Gln
                165                 170                 175

Val Phe Arg Gly Val His Gly Leu Arg Phe Arg Pro Ala Gly Pro Arg
            180                 185                 190

Ala Thr Val Arg Leu Gly Gly Phe Ala Ser Ala Ser Leu Lys His Val
        195                 200                 205

Ala Ala Gln Gln Phe Gly Glu Asp Thr Phe Phe Gly Ile Trp Thr Cys
    210                 215                 220

Leu Gly Ala Pro Ile Lys Gly Tyr Ser Phe Phe Pro Gly Glu Glu Glu
225                 230                 235                 240

Val Leu Ile Pro Pro Phe Glu Thr Phe Gln Val Ile Asn Ala Ser Arg
                245                 250                 255

Leu Ala Gln Gly Pro Ala Arg Ile Tyr Leu Arg Ala Leu Gly Lys His
            260                 265                 270

Ser Thr Tyr Asn Cys Glu Tyr Ile Lys Asp Lys Lys Cys Lys Ser Gly
        275                 280                 285

Pro Cys His Leu Asp Asn Ser Ala Met Gly Gln Ser Pro Leu Ser Ala
    290                 295                 300

Val Trp Ser Leu Leu Leu Leu Leu Trp Phe Leu Val Val Arg Ala Phe
305                 310                 315                 320

Pro Asp Gly Pro Gly Leu Leu
                325
```

<210> SEQ ID NO 2
<211> LENGTH: 41
<212> TYPE: PRT
<213> ORGANISM: Homo sapiens

<400> SEQUENCE: 2

```
Glu Ala Leu Gln Leu Leu Gly Ser Gly Gln Arg Pro Pro Arg Cys His
1               5                   10                  15

Gln Val Phe Arg Gly Val His Gly Leu Arg Phe Arg Pro Ala Gly Pro
            20                  25                  30
```

Arg Ala Thr Val Arg Leu Gly Gly Phe
35 40

<210> SEQ ID NO 3
<211> LENGTH: 41
<212> TYPE: PRT
<213> ORGANISM: Homo sapiens

<400> SEQUENCE: 3

Gly Val His Gly Leu Arg Phe Arg Pro Ala Gly Pro Arg Ala Thr Val
1 5 10 15

Arg Leu Gly Gly Phe Ala Ser Ala Ser Leu Lys His Val Ala Ala Gln
20 25 30

Gln Phe Gly Glu Asp Thr Phe Phe Gly
35 40

<210> SEQ ID NO 4
<211> LENGTH: 41
<212> TYPE: PRT
<213> ORGANISM: Homo sapiens

<400> SEQUENCE: 4

Gly Ile Trp Thr Cys Leu Gly Ala Pro Ile Lys Gly Tyr Ser Phe Phe
1 5 10 15

Pro Gly Glu Glu Glu Val Leu Ile Pro Pro Phe Glu Thr Phe Gln Val
20 25 30

Ile Asn Ala Ser Arg Leu Ala Gln Gly
35 40

<210> SEQ ID NO 5
<211> LENGTH: 117
<212> TYPE: PRT
<213> ORGANISM: Rattus norvegicus

<400> SEQUENCE: 5

Glu Val Gln Leu Val Glu Ser Gly Gly Gly Leu Val Gln Pro Gly Arg
1 5 10 15

Ser Leu Lys Leu Ser Cys Ala Ala Ser Gly Phe Thr Phe Ser Asn Phe
20 25 30

Ala Met Ala Trp Val Arg Gln Ala Pro Thr Lys Gly Leu Glu Trp Val
35 40 45

Ala Ser Ile Ser Tyr Asp Gly Val Asn Thr Tyr Tyr Arg Asp Ser Val
50 55 60

Lys Gly Arg Phe Thr Ile Ser Arg Asn Thr Ala Lys Ser Ser Leu Tyr
65 70 75 80

Leu Gln Met Asp Ser Leu Arg Ser Glu Asp Thr Ser Thr Tyr Phe Cys
85 90 95

Ala Lys Arg Gly Ala Ala Pro Phe Asp Phe Trp Gly Gln Gly Val Met
100 105 110

Val Thr Val Ser Ser
115

<210> SEQ ID NO 6
<211> LENGTH: 106
<212> TYPE: PRT
<213> ORGANISM: Rattus norvegicus

<400> SEQUENCE: 6

```
Glu Ile Val Leu Thr Gln Ser Pro Thr Thr Met Thr Ala Ser Pro Gly
1               5                   10                  15

Glu Lys Val Thr Ile Thr Cys Arg Ala Ser Ser Ser Val Ser Tyr Met
            20                  25                  30

Tyr Trp Tyr Gln Gln Lys Pro Gly Ala Ser Pro Lys Pro Trp Ile Tyr
        35                  40                  45

Glu Thr Ser Lys Leu Ala Ser Gly Val Pro Asp Arg Phe Ser Gly Ser
    50                  55                  60

Gly Ser Gly Thr Ser Tyr Ser Leu Thr Ile Asn Asn Met Glu Ala Glu
65                  70                  75                  80

Asp Ala Ala Thr Tyr Tyr Cys Gln Gln Trp Asn Tyr Pro Ser Cys Thr
                85                  90                  95

Phe Gly Ala Gly Thr Lys Leu Glu Leu Lys
            100                 105
```

<210> SEQ ID NO 7
<211> LENGTH: 240
<212> TYPE: PRT
<213> ORGANISM: Rattus norvegicus

<400> SEQUENCE: 7

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Phe
            20                  25                  30

Ala Met Ala Trp Val Arg Gln Ala Pro Thr Lys Gly Leu Glu Trp Val
        35                  40                  45

Ala Ser Ile Ser Tyr Asp Gly Val Asn Thr Tyr Tyr Arg Asp Ser Val
    50                  55                  60

Lys Gly Arg Phe Thr Ile Ser Arg Asn Thr Ala Lys Ser Ser Leu Tyr
65                  70                  75                  80

Leu Gln Met Asp Ser Leu Arg Ser Glu Asp Thr Ser Thr Tyr Phe Cys
                85                  90                  95

Ala Lys Arg Gly Ala Ala Pro Phe Asp Phe Trp Gly Gln Gly Val Met
            100                 105                 110

Val Thr Val Ser Ser Leu Glu Gly Gly Gly Gly Ser Gly Gly Gly Gly
        115                 120                 125

Ser Gly Gly Gly Ala Ser Glu Ile Val Leu Thr Gln Ser Pro Thr Thr
    130                 135                 140

Met Thr Ala Ser Pro Gly Glu Lys Val Thr Ile Thr Cys Arg Ala Ser
145                 150                 155                 160

Ser Ser Val Ser Tyr Met Tyr Trp Tyr Gln Gln Lys Pro Gly Ala Ser
                165                 170                 175

Pro Lys Pro Trp Ile Tyr Glu Thr Ser Lys Leu Ala Ser Gly Val Pro
            180                 185                 190

Asp Arg Phe Ser Gly Ser Gly Ser Gly Thr Ser Tyr Ser Leu Thr Ile
        195                 200                 205

Asn Asn Met Glu Ala Glu Asp Ala Ala Thr Tyr Tyr Cys Gln Gln Trp
    210                 215                 220

Asn Tyr Pro Ser Cys Thr Phe Gly Ala Gly Thr Lys Leu Glu Leu Ala
225                 230                 235                 240
```

<210> SEQ ID NO 8

<211> LENGTH: 123
<212> TYPE: PRT
<213> ORGANISM: Rattus norvegicus

<400> SEQUENCE: 8

```
Glu Val Gln Leu Val Glu Ser Gly Gly Gly Leu Val Gln Pro Gly Arg
1               5                   10                  15

Ser Leu Lys Leu Ser Cys Ala Val Ser Gly Phe Thr Phe Ser Asp Tyr
            20                  25                  30

Ala Met Val Trp Val Arg Gln Ala Pro Lys Arg Gly Leu Glu Trp Val
        35                  40                  45

Ala Thr Ile Thr Tyr Asp Gly Ser Arg Ile Tyr Tyr Arg Asp Ser Val
    50                  55                  60

Lys Gly Arg Phe Thr Ile Ser Arg Asp Asn Ala Asn Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Gln Gly Gly Tyr Thr Thr Asp Tyr Tyr Tyr Val Met Asp Ala
            100                 105                 110

Trp Gly Gln Gly Thr Ser Val Thr Val Ser Ser
        115                 120
```

<210> SEQ ID NO 9
<211> LENGTH: 106
<212> TYPE: PRT
<213> ORGANISM: Rattus norvegicus

<400> SEQUENCE: 9

```
Asp Val Val Leu Thr Gln Ser Pro Thr Thr Met Ala Ala Ser Pro Gly
1               5                   10                  15

Gly Lys Val Thr Leu Thr Cys Arg Ala Ser Ser Gly Val Ser Tyr Met
            20                  25                  30

Ala Trp Tyr Gln Gln Lys Pro Gly Asp Ser Pro Lys Leu Trp Ile Tyr
        35                  40                  45

Gly Thr Ser Lys Leu Ala Ser Gly Val Pro Asn Arg Phe Thr Ala Gly
    50                  55                  60

Gly Ser Gly Thr Ser Tyr Ser Leu Ile Ile Ser Ser Met Glu Thr Glu
65                  70                  75                  80

Asp Val Ala Thr Tyr Tyr Cys Gln Gln Cys Cys Ser Thr Pro Leu Thr
                85                  90                  95

Phe Gly Ser Gly Thr Lys Leu Glu Ile Lys
            100                 105
```

<210> SEQ ID NO 10
<211> LENGTH: 249
<212> TYPE: PRT
<213> ORGANISM: Rattus norvegicus

<400> SEQUENCE: 10

```
Glu Val Gln Leu Val Glu Ser Gly Gly Gly Leu Val Gln Pro Gly Arg
1               5                   10                  15

Ser Leu Lys Leu Ser Cys Ala Val Ser Gly Phe Thr Phe Ser Asp Tyr
            20                  25                  30

Ala Met Val Trp Val Arg Gln Ala Pro Lys Arg Gly Leu Glu Trp Val
        35                  40                  45

Ala Thr Ile Thr Tyr Asp Gly Ser Arg Ile Tyr Tyr Arg Asp Ser Val
    50                  55                  60
```

-continued

Lys Gly Arg Phe Thr Ile Ser Arg Asp Asn Ala Asn Ser Thr Leu Tyr
65 70 75 80

Leu Gln Met Asp Ser Leu Arg Ser Glu Asp Thr Ala Thr Tyr Tyr Cys
85 90 95

Ala Arg Gln Gly Gly Tyr Thr Thr Asp Tyr Tyr Tyr Val Met Asp Ala
100 105 110

Trp Gly Gln Gly Thr Ser Val Thr Val Ser Ser Leu Glu Gly Gly Gly
115 120 125

Gly Ser Gly Gly Gly Gly Ser Gly Gly Gly Ala Ser Asp Val Val Leu
130 135 140

Thr Gln Ser Pro Thr Thr Met Ala Ala Ser Pro Gly Gly Lys Val Thr
145 150 155 160

Leu Thr Cys Arg Ala Ser Ser Gly Val Ser Tyr Met Ala Trp Tyr Gln
165 170 175

Gln Lys Pro Gly Asp Ser Pro Lys Leu Trp Ile Tyr Gly Thr Ser Lys
180 185 190

Leu Ala Ser Gly Val Pro Asn Arg Phe Thr Ala Gly Gly Ser Gly Thr
195 200 205

Ser Tyr Ser Leu Ile Ile Ser Ser Met Glu Thr Glu Asp Val Ala Thr
210 215 220

Tyr Tyr Cys Gln Gln Cys Cys Ser Thr Pro Leu Thr Phe Gly Ser Gly
225 230 235 240

Thr Lys Leu Glu Ile Lys Ala Ala Ala
245

<210> SEQ ID NO 11
<211> LENGTH: 123
<212> TYPE: PRT
<213> ORGANISM: Rattus norvegicus

<400> SEQUENCE: 11

Glu Val Leu Leu Val Glu Ser Gly Gly Gly Leu Val Gln Pro Gly Arg
1 5 10 15

Ser Met Lys Leu Ser Cys Ala Ala Ser Gly Phe Thr Phe Ser Asp Phe
20 25 30

Pro Met Ala Trp Val Arg Leu Thr Pro Thr Arg Gly Leu Glu Trp Val
35 40 45

Ala Thr Ile Ser Thr Gly Gly Gly Thr Thr Tyr Tyr Arg Gly Ser Val
50 55 60

Lys Gly Arg Phe Thr Ile Ser Arg Asp Asn Ala Glu Ser Thr Leu Tyr
65 70 75 80

Leu Gln Met Asn Ser Leu Lys Ser Glu Asp Thr Ala Thr Tyr Phe Cys
85 90 95

Thr Ser Pro Leu Tyr Tyr Ser Asn Tyr Val Gly Asn Val Met Asp Ala
100 105 110

Trp Gly Gln Gly Ala Ser Val Thr Val Ser Ser
115 120

<210> SEQ ID NO 12
<211> LENGTH: 113
<212> TYPE: PRT
<213> ORGANISM: Rattus norvegicus

<400> SEQUENCE: 12

Asp Ile Val Met Thr Gln Ser Pro Phe Ser Leu Ala Val Ser Val Gly
1 5 10 15

```
Glu Met Val Thr Ile Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Tyr Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Asp Val Gln Ala Glu Asp Leu Ala Asp Tyr Tyr Cys Leu Gln
                85                  90                  95

His Tyr Ile Ser Pro Phe Thr Phe Gly Ser Gly Thr Lys Phe Glu Ile
            100                 105                 110

Lys


<210> SEQ ID NO 13
<211> LENGTH: 259
<212> TYPE: PRT
<213> ORGANISM: Rattus norvegicus

<400> SEQUENCE: 13

Met Ala Glu Val Leu Leu Val Glu Ser Gly Gly Gly Leu Val Gln Pro
1               5                   10                  15

Gly Arg Ser Met Lys Leu Ser Cys Ala Ala Ser Gly Phe Thr Phe Ser
            20                  25                  30

Asp Phe Pro Met Ala Trp Val Arg Leu Thr Pro Thr Arg Gly Leu Glu
        35                  40                  45

Trp Val Ala Thr Ile Ser Thr Gly Gly Gly Thr Thr Tyr Tyr Arg Gly
    50                  55                  60

Ser Val Lys Gly Arg Phe Thr Ile Ser Arg Asp Asn Ala Glu Ser Thr
65                  70                  75                  80

Leu Tyr Leu Gln Met Asn Ser Leu Lys Ser Glu Asp Thr Ala Thr Tyr
                85                  90                  95

Phe Cys Thr Ser Pro Leu Tyr Tyr Ser Asn Tyr Val Gly Asn Val Met
            100                 105                 110

Asp Ala Trp Gly Gln Gly Ala Ser Val Thr Val Ser Ser Leu Glu Gly
        115                 120                 125

Gly Gly Gly Ser Gly Gly Gly Gly Ser Gly Gly Gly Ala Ser Asp Ile
    130                 135                 140

Val Met Thr Gln Ser Pro Phe Ser Leu Ala Val Ser Val Gly Glu Met
145                 150                 155                 160

Val Thr Ile Asn Cys Lys Ser Ser Gln Ser Leu Leu Ser Ser Gly Asn
                165                 170                 175

Gln Lys Asn Tyr Leu Ala Trp Tyr Gln Gln Lys Pro Gly Gln Ser Pro
            180                 185                 190

Lys Leu Leu Ile Tyr Tyr Ala Ser Thr Arg Gln Ser Gly Val Pro Asp
        195                 200                 205

Arg Phe Ile Gly Ser Gly Ser Gly Thr Asp Phe Thr Leu Thr Ile Ser
    210                 215                 220

Asp Val Gln Ala Glu Asp Leu Ala Asp Tyr Tyr Cys Leu Gln His Tyr
225                 230                 235                 240

Ile Ser Pro Phe Thr Phe Gly Ser Gly Thr Lys Phe Glu Ile Lys Ala
                245                 250                 255

Ala Ala Val
```

<210> SEQ ID NO 14
<211> LENGTH: 116
<212> TYPE: PRT
<213> ORGANISM: Rattus norvegicus

<400> SEQUENCE: 14

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ile Asn
            20                  25                  30

Tyr Trp Asp Trp Ile Arg Lys Phe Pro Gly Asn Lys Met Glu Trp Ile
        35                  40                  45

Gly His Ile Asn Tyr Ser Gly Gly Thr Asn Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Val
                85                  90                  95

Ser Glu Gly Ala Gly Gly Leu Asp Tyr Trp Gly Gln Gly Val Met Val
            100                 105                 110

Thr Val Ser Ser
        115
```

<210> SEQ ID NO 15
<211> LENGTH: 110
<212> TYPE: PRT
<213> ORGANISM: Rattus norvegicus

<400> SEQUENCE: 15

```
Asp Ile Val Leu Thr Gln Ser Pro Ala Leu Ala Val Ser Leu Glu Gln
1               5                   10                  15

Arg Ala Thr Ile Ser Cys Lys Thr Ser Gln Asn Val Asp Tyr Tyr Gly
            20                  25                  30

Ile Thr Tyr Met His Trp Tyr Gln Gln Lys Pro Arg His His Pro Lys
        35                  40                  45

Leu Leu Ile Tyr Glu Gly Ser Asn Leu Pro Ser Gly Ile Pro Ala Arg
    50                  55                  60

Phe Ser Gly Ser Gly Ser Gly Thr Asp Phe Thr Leu Thr Ile Asp Pro
65                  70                  75                  80

Val Glu Ala Asp Asp Val Ala Thr Tyr Tyr Cys Gln Gln Ser Lys Asp
                85                  90                  95

Tyr Pro Trp Thr Phe Gly Gly Gly Thr Lys Leu Glu Leu Lys
            100                 105                 110
```

<210> SEQ ID NO 16
<211> LENGTH: 248
<212> TYPE: PRT
<213> ORGANISM: Rattus norvegicus

<400> SEQUENCE: 16

```
Met Ala Glu Val Gln Leu Gln Glu Ser Gly Pro Gly Leu Val Lys Pro
1               5                   10                  15

Ser Gln Ser Leu Ser Leu Thr Cys Ser Val Thr Gly Tyr Ser Ile Thr
            20                  25                  30

Ile Asn Tyr Trp Asp Trp Ile Arg Lys Phe Pro Gly Asn Lys Met Glu
        35                  40                  45

Trp Ile Gly His Ile Asn Tyr Ser Gly Gly Thr Asn Tyr Asn Pro Ser
    50                  55                  60
```

Leu Lys Ser Arg Ile Ser Ile Thr Arg Asp Thr Ser Lys Asn Gln Phe
65 70 75 80

Phe Leu Gln Leu Asn Ser Val Thr Thr Glu Asp Thr Ala Thr Tyr Tyr
85 90 95

Cys Val Ser Glu Gly Ala Gly Gly Leu Asp Tyr Trp Gly Gln Gly Val
100 105 110

Met Val Thr Val Ser Ser Leu Glu Gly Gly Gly Gly Ser Gly Gly Gly
115 120 125

Gly Ser Gly Gly Gly Ala Ser Asp Ile Val Leu Thr Gln Ser Pro Ala
130 135 140

Leu Ala Val Ser Leu Glu Gln Arg Ala Thr Ile Ser Cys Lys Thr Ser
145 150 155 160

Gln Asn Val Asp Tyr Tyr Gly Ile Thr Tyr Met His Trp Tyr Gln Gln
165 170 175

Lys Pro Arg His His Pro Lys Leu Leu Ile Tyr Glu Gly Ser Asn Leu
180 185 190

Pro Ser Gly Ile Pro Ala Arg Phe Ser Gly Ser Gly Ser Gly Thr Asp
195 200 205

Phe Thr Leu Thr Ile Asp Pro Val Glu Ala Asp Asp Val Ala Thr Tyr
210 215 220

Tyr Cys Gln Gln Ser Lys Asp Tyr Pro Trp Thr Phe Gly Gly Gly Thr
225 230 235 240

Lys Leu Glu Leu Lys Ala Ala Ala
245

<210> SEQ ID NO 17
<211> LENGTH: 121
<212> TYPE: PRT
<213> ORGANISM: Rattus norvegicus

<400> SEQUENCE: 17

Glu Val Gln Leu Val Glu Ser Gly Gly Gly Leu Val Gln Pro Gly Arg
1 5 10 15

Ser Met Lys Leu Ser Cys Ala Ala Ser Gly Phe Thr Phe Ser Asn Phe
20 25 30

Pro Met Ala Trp Val Arg Gln Ala Pro Thr Lys Gly Leu Glu Trp Val
35 40 45

Ala Val Val Ser Ile Ser Gly Gly Ala Thr Tyr Tyr Arg Asp Ser Val
50 55 60

Arg Gly Arg Phe Thr Ile Ser Arg His Asn Ala Thr Gly Thr Leu Tyr
65 70 75 80

Leu His Met Asn Ser Leu Arg Ser Glu Asp Thr Ala Thr Tyr Tyr Cys
85 90 95

Val Arg Gly Asp Gly Ser Ser Arg Gly Tyr Tyr Phe Asp Tyr Trp Gly
100 105 110

Gln Gly Val Met Val Thr Val Ser Ser
115 120

<210> SEQ ID NO 18
<211> LENGTH: 107
<212> TYPE: PRT
<213> ORGANISM: Rattus norvegicus

<400> SEQUENCE: 18

Glu Ile Val Leu Thr Gln Ser Pro Thr Ala Ile Pro Val Ser Pro Gly
1 5 10 15

```
Glu Lys Val Thr Ile Thr Cys Arg Ala Ser Ser Ser Val Ser Tyr Met
            20                  25                  30

Tyr Trp Tyr Gln Gln Lys Ser Gly Ala Ser Pro Lys Leu Trp Ile Tyr
        35                  40                  45

Asp Thr Ser Lys Leu Ala Ser Gly Val Pro Asn Arg Phe Ser Gly Ser
    50                  55                  60

Gly Ser Gly Thr Ser Tyr Ser Leu Thr Ile Asn Thr Met Glu Thr Glu
65                  70                  75                  80

Asp Gly Ala Thr Tyr Tyr Cys Gln Gln Trp Ser Ser Ser Pro Ser Met
                85                  90                  95

Thr Phe Gly Gly Gly Thr Lys Leu Glu Leu Lys
            100                 105


<210> SEQ ID NO 19
<211> LENGTH: 250
<212> TYPE: PRT
<213> ORGANISM: Rattus norvegicus

<400> SEQUENCE: 19

Met Ala Glu Val Gln Leu Val Glu Ser Gly Gly Gly Leu Val Gln Pro
1               5                   10                  15

Gly Arg Ser Met Lys Leu Ser Cys Ala Ala Ser Gly Phe Thr Phe Ser
            20                  25                  30

Asn Phe Pro Met Ala Trp Val Arg Gln Ala Pro Thr Lys Gly Leu Glu
        35                  40                  45

Trp Val Ala Val Val Ser Ile Ser Gly Gly Ala Thr Tyr Tyr Arg Asp
    50                  55                  60

Ser Val Arg Gly Arg Phe Thr Ile Ser Arg His Asn Ala Thr Gly Thr
65                  70                  75                  80

Leu Tyr Leu His Met Asn Ser Leu Arg Ser Glu Asp Thr Ala Thr Tyr
                85                  90                  95

Tyr Cys Val Arg Gly Asp Gly Ser Ser Arg Gly Tyr Tyr Phe Asp Tyr
            100                 105                 110

Trp Gly Gln Gly Val Met Val Thr Val Ser Ser Leu Glu Gly Gly Gly
        115                 120                 125

Gly Ser Gly Gly Gly Gly Ser Gly Gly Gly Ala Ser Glu Ile Val Leu
    130                 135                 140

Thr Gln Ser Pro Thr Ala Ile Pro Val Ser Pro Gly Glu Lys Val Thr
145                 150                 155                 160

Ile Thr Cys Arg Ala Ser Ser Ser Val Ser Tyr Met Tyr Trp Tyr Gln
                165                 170                 175

Gln Lys Ser Gly Ala Ser Pro Lys Leu Trp Ile Tyr Asp Thr Ser Lys
            180                 185                 190

Leu Ala Ser Gly Val Pro Asn Arg Phe Ser Gly Ser Gly Ser Gly Thr
        195                 200                 205

Ser Tyr Ser Leu Thr Ile Asn Thr Met Glu Thr Glu Asp Gly Ala Thr
    210                 215                 220

Tyr Tyr Cys Gln Gln Trp Ser Ser Ser Pro Ser Met Thr Phe Gly Gly
225                 230                 235                 240

Gly Thr Lys Leu Glu Leu Lys Ala Ala Ala
                245                 250


<210> SEQ ID NO 20
<211> LENGTH: 10
<212> TYPE: PRT
```

<213> ORGANISM: Rattus norvegicus

<400> SEQUENCE: 20

Arg Ala Ser Ser Ser Val Ser Tyr Met Tyr
1 5 10

<210> SEQ ID NO 21
<211> LENGTH: 10
<212> TYPE: PRT
<213> ORGANISM: Rattus norvegicus

<400> SEQUENCE: 21

Arg Ala Ser Ser Gly Val Ser Tyr Met Ala
1 5 10

<210> SEQ ID NO 22
<211> LENGTH: 17
<212> TYPE: PRT
<213> ORGANISM: Rattus norvegicus

<400> SEQUENCE: 22

Lys Ser Ser Gln Ser Leu Leu Ser Ser Gly Asn Gln Lys Asn Tyr Leu
1 5 10 15

Ala

<210> SEQ ID NO 23
<211> LENGTH: 15
<212> TYPE: PRT
<213> ORGANISM: Rattus norvegicus

<400> SEQUENCE: 23

Lys Thr Ser Gln Asn Val Asp Tyr Tyr Gly Ile Thr Tyr Met His
1 5 10 15

<210> SEQ ID NO 24
<211> LENGTH: 10
<212> TYPE: PRT
<213> ORGANISM: Rattus norvegicus

<400> SEQUENCE: 24

Arg Ala Ser Ser Ser Val Ser Tyr Met Tyr
1 5 10

<210> SEQ ID NO 25
<211> LENGTH: 7
<212> TYPE: PRT
<213> ORGANISM: Rattus norvegicus

<400> SEQUENCE: 25

Glu Thr Ser Lys Leu Ala Ser
1 5

<210> SEQ ID NO 26
<211> LENGTH: 7
<212> TYPE: PRT
<213> ORGANISM: Rattus norvegicus

<400> SEQUENCE: 26

Gly Thr Ser Lys Leu Ala Ser
1 5

<210> SEQ ID NO 27
<211> LENGTH: 7
<212> TYPE: PRT

<213> ORGANISM: Rattus norvegicus

<400> SEQUENCE: 27

Tyr Ala Ser Thr Arg Gln Ser
1 5

<210> SEQ ID NO 28
<211> LENGTH: 7
<212> TYPE: PRT
<213> ORGANISM: Rattus norvegicus

<400> SEQUENCE: 28

Glu Gly Ser Asn Leu Pro Ser
1 5

<210> SEQ ID NO 29
<211> LENGTH: 7
<212> TYPE: PRT
<213> ORGANISM: Rattus norvegicus

<400> SEQUENCE: 29

Asp Thr Ser Lys Leu Ala Ser
1 5

<210> SEQ ID NO 30
<211> LENGTH: 9
<212> TYPE: PRT
<213> ORGANISM: Rattus norvegicus

<400> SEQUENCE: 30

Gln Gln Trp Asn Tyr Pro Ser Cys Thr
1 5

<210> SEQ ID NO 31
<211> LENGTH: 9
<212> TYPE: PRT
<213> ORGANISM: Rattus norvegicus

<400> SEQUENCE: 31

Gln Gln Cys Cys Ser Thr Pro Leu Thr
1 5

<210> SEQ ID NO 32
<211> LENGTH: 9
<212> TYPE: PRT
<213> ORGANISM: Rattus norvegicus

<400> SEQUENCE: 32

Leu Gln His Tyr Ile Ser Pro Phe Thr
1 5

<210> SEQ ID NO 33
<211> LENGTH: 9
<212> TYPE: PRT
<213> ORGANISM: Rattus norvegicus

<400> SEQUENCE: 33

Gln Gln Ser Lys Asp Tyr Pro Trp Thr
1 5

<210> SEQ ID NO 34
<211> LENGTH: 10
<212> TYPE: PRT
<213> ORGANISM: Rattus norvegicus

<400> SEQUENCE: 34

Gln Gln Trp Ser Ser Ser Pro Ser Met Thr
1 5 10

<210> SEQ ID NO 35
<211> LENGTH: 5
<212> TYPE: PRT
<213> ORGANISM: Rattus norvegicus

<400> SEQUENCE: 35

Asn Phe Ala Met Ala
1 5

<210> SEQ ID NO 36
<211> LENGTH: 5
<212> TYPE: PRT
<213> ORGANISM: Rattus norvegicus

<400> SEQUENCE: 36

Asp Tyr Ala Met Val
1 5

<210> SEQ ID NO 37
<211> LENGTH: 5
<212> TYPE: PRT
<213> ORGANISM: Rattus norvegicus

<400> SEQUENCE: 37

Asp Phe Pro Met Ala
1 5

<210> SEQ ID NO 38
<211> LENGTH: 5
<212> TYPE: PRT
<213> ORGANISM: Rattus norvegicus

<400> SEQUENCE: 38

Ile Asn Tyr Trp Asp
1 5

<210> SEQ ID NO 39
<211> LENGTH: 5
<212> TYPE: PRT
<213> ORGANISM: Rattus norvegicus

<400> SEQUENCE: 39

Asn Phe Pro Met Ala
1 5

<210> SEQ ID NO 40
<211> LENGTH: 13
<212> TYPE: PRT
<213> ORGANISM: Rattus norvegicus

<400> SEQUENCE: 40

Ser Ile Ser Tyr Asp Gly Val Asn Thr Tyr Tyr Arg Asp
1 5 10

<210> SEQ ID NO 41
<211> LENGTH: 13
<212> TYPE: PRT
<213> ORGANISM: Rattus norvegicus

<400> SEQUENCE: 41

Thr Ile Thr Tyr Asp Gly Ser Arg Ile Tyr Tyr Arg Asp
1               5                   10

<210> SEQ ID NO 42
<211> LENGTH: 13
<212> TYPE: PRT
<213> ORGANISM: Rattus norvegicus

<400> SEQUENCE: 42

Thr Ile Ser Thr Gly Gly Gly Thr Thr Tyr Tyr Arg Gly
1               5                   10

<210> SEQ ID NO 43
<211> LENGTH: 12
<212> TYPE: PRT
<213> ORGANISM: Rattus norvegicus

<400> SEQUENCE: 43

His Ile Asn Tyr Ser Gly Gly Thr Asn Tyr Asn Pro
1               5                   10

<210> SEQ ID NO 44
<211> LENGTH: 13
<212> TYPE: PRT
<213> ORGANISM: Rattus norvegicus

<400> SEQUENCE: 44

Val Val Ser Ile Ser Gly Gly Ala Thr Tyr Tyr Arg Asp
1               5                   10

<210> SEQ ID NO 45
<211> LENGTH: 8
<212> TYPE: PRT
<213> ORGANISM: Rattus norvegicus

<400> SEQUENCE: 45

Arg Gly Ala Ala Pro Phe Asp Phe
1               5

<210> SEQ ID NO 46
<211> LENGTH: 14
<212> TYPE: PRT
<213> ORGANISM: Rattus norvegicus

<400> SEQUENCE: 46

Gln Gly Gly Tyr Thr Thr Asp Tyr Tyr Tyr Val Met Asp Ala
1               5                   10

<210> SEQ ID NO 47
<211> LENGTH: 14
<212> TYPE: PRT
<213> ORGANISM: Rattus norvegicus

<400> SEQUENCE: 47

Pro Leu Tyr Tyr Ser Asn Tyr Val Gly Asn Val Met Asp Ala
1               5                   10

<210> SEQ ID NO 48
<211> LENGTH: 8
<212> TYPE: PRT
<213> ORGANISM: Rattus norvegicus

<400> SEQUENCE: 48

Glu Gly Ala Gly Gly Leu Asp Tyr
1               5

<210> SEQ ID NO 49
<211> LENGTH: 12
<212> TYPE: PRT
<213> ORGANISM: Rattus norvegicus

<400> SEQUENCE: 49

Gly Asp Gly Ser Ser Arg Gly Tyr Tyr Phe Asp Tyr
1               5                   10

<210> SEQ ID NO 50
<211> LENGTH: 11
<212> TYPE: PRT
<213> ORGANISM: Rattus norvegicus

<400> SEQUENCE: 50

Glu Thr Ser Lys Leu Ala Ser Gly Val Pro Asp
1               5                   10

<210> SEQ ID NO 51
<211> LENGTH: 11
<212> TYPE: PRT
<213> ORGANISM: Rattus norvegicus

<400> SEQUENCE: 51

Gly Thr Ser Lys Leu Ala Ser Gly Val Pro Asn
1               5                   10

<210> SEQ ID NO 52
<211> LENGTH: 11
<212> TYPE: PRT
<213> ORGANISM: Rattus norvegicus

<400> SEQUENCE: 52

Tyr Ala Ser Thr Arg Gln Ser Gly Val Pro Asp
1               5                   10

<210> SEQ ID NO 53
<211> LENGTH: 11
<212> TYPE: PRT
<213> ORGANISM: Rattus norvegicus

<400> SEQUENCE: 53

Glu Gly Ser Asn Leu Pro Ser Gly Ile Pro Ala
1               5                   10

<210> SEQ ID NO 54
<211> LENGTH: 11
<212> TYPE: PRT
<213> ORGANISM: Rattus norvegicus

<400> SEQUENCE: 54

Asp Thr Ser Lys Leu Ala Ser Gly Val Pro Asn
1               5                   10

<210> SEQ ID NO 55
<211> LENGTH: 17
<212> TYPE: PRT
<213> ORGANISM: Rattus norvegicus

```
<400> SEQUENCE: 55

Ser Ile Ser Tyr Asp Gly Val Asn Thr Tyr Tyr Arg Asp Ser Val Lys
1               5                   10                  15

Gly


<210> SEQ ID NO 56
<211> LENGTH: 17
<212> TYPE: PRT
<213> ORGANISM: Rattus norvegicus

<400> SEQUENCE: 56

Thr Ile Thr Tyr Asp Gly Ser Arg Ile Tyr Tyr Arg Asp Ser Val Lys
1               5                   10                  15

Gly


<210> SEQ ID NO 57
<211> LENGTH: 17
<212> TYPE: PRT
<213> ORGANISM: Rattus norvegicus

<400> SEQUENCE: 57

Thr Ile Ser Thr Gly Gly Gly Thr Thr Tyr Tyr Arg Gly Ser Val Lys
1               5                   10                  15

Gly


<210> SEQ ID NO 58
<211> LENGTH: 16
<212> TYPE: PRT
<213> ORGANISM: Rattus norvegicus

<400> SEQUENCE: 58

His Ile Asn Tyr Ser Gly Gly Thr Asn Tyr Asn Pro Ser Leu Lys Ser
1               5                   10                  15


<210> SEQ ID NO 59
<211> LENGTH: 17
<212> TYPE: PRT
<213> ORGANISM: Rattus norvegicus

<400> SEQUENCE: 59

Val Val Ser Ile Ser Gly Gly Ala Thr Tyr Tyr Arg Asp Ser Val Arg
1               5                   10                  15

Gly
```